(12) United States Patent
Doucet

(10) Patent No.: US 11,273,389 B2
(45) Date of Patent: *Mar. 15, 2022

(54) SYSTEM AND PROCESS FOR EXTRACTION OF PRODUCTS FROM APPLE PEEL

(71) Applicant: LEAHY ORCHARDS INC., Franklin Centre (CA)

(72) Inventor: Jocelyn Doucet, Montreal (CA)

(73) Assignee: LEAHY ORCHARDS INC., Franklin Centre (CA)

(*) Notice: Subject to any disclaimer, the term of this patent is extended or adjusted under 35 U.S.C. 154(b) by 1 day.

This patent is subject to a terminal disclaimer.

(21) Appl. No.: 16/855,553

(22) Filed: Apr. 22, 2020

(65) Prior Publication Data

US 2020/0246720 A1    Aug. 6, 2020

Related U.S. Application Data

(63) Continuation of application No. 15/960,710, filed on Apr. 24, 2018, now Pat. No. 10,668,402, which is a
(Continued)

(51) Int. Cl.
*A23L 2/04* (2006.01)
*A23L 5/00* (2016.01)
(Continued)

(52) U.S. Cl.
CPC ............ *B01D 11/0284* (2013.01); *A23L 2/02* (2013.01); *A23L 2/04* (2013.01); *A23L 5/00* (2016.08);
(Continued)

(58) Field of Classification Search
CPC ............ B01D 11/0284; B01D 11/0283; B01D 11/0269; B01D 61/145; B01D 2011/002;
(Continued)

(56) References Cited

U.S. PATENT DOCUMENTS 3,189,266 A    6/1965   Palmqvist
3,862,347 A    1/1975   Thijssen
(Continued)

FOREIGN PATENT DOCUMENTS

EP    1233988 B1    3/2007
GB    2079176 A     1/1982
(Continued)

OTHER PUBLICATIONS

International Search Report of PCT/CA2013/000726; dated Dec. 20, 2013; Emman Ben Jamil.
(Continued)

*Primary Examiner* — Benjamin L Lebron
(74) *Attorney, Agent, or Firm* — Benoit & Cote, Inc.; Mathieu Miron

(57) ABSTRACT

The present document describes a system and a process for the extraction of several products from apple peel. There are several unit operations involved including an ultrafiltration unit, concentration unit, and a three stage counter current separator centrifuge wherein water is used as the solvent. The final products that are extracted from apple peel include pectin, syrup, fibers, as well as soluble and dried retentate fractions.

24 Claims, 7 Drawing Sheets

Related U.S. Application Data continuation of application No. 14/422,712, filed as application No. PCT/CA2013/000726 on Aug. 16, 2013, now Pat. No. 9,981,204.

(60) Provisional application No. 61/691,049, filed on Aug. 20, 2012.

(51) Int. Cl.
| | |
|---|---|
| *A23L 19/00* | (2016.01) |
| *A23L 29/30* | (2016.01) |
| *A23L 33/105* | (2016.01) |
| *A61K 36/73* | (2006.01) |
| *B01D 11/02* | (2006.01) |
| *B01D 11/00* | (2006.01) |
| *C13B 20/16* | (2011.01) |
| *C13K 11/00* | (2006.01) |
| *C13K 13/00* | (2006.01) |
| *A23L 2/02* | (2006.01) |
| *B01D 61/14* | (2006.01) |

(52) U.S. Cl.
CPC ............... *A23L 19/09* (2016.08); *A23L 29/30* (2016.08); *A23L 33/105* (2016.08); *A61K 36/73* (2013.01); *B01D 11/02* (2013.01); *B01D 11/0238* (2013.01); *B01D 11/0269* (2013.01); *B01D 61/145* (2013.01); *C13B 20/165* (2013.01); *C13K 11/00* (2013.01); *C13K 13/00* (2013.01); *C13K 13/007* (2013.01); *A23V 2250/2116* (2013.01); *A23V 2250/2132* (2013.01); *B01D 2011/002* (2013.01)

(58) Field of Classification Search
CPC ... A23L 19/09; A23L 2/02; A23L 2/04; A23L 33/105; A23L 5/00; C13B 20/165; C13K 11/00; C13K 13/00; C13K 13/007; A61K 36/73; A23V 2250/2116; A23V 2250/2132

See application file for complete search history.

(56) References Cited

U.S. PATENT DOCUMENTS

| | | | |
|---|---|---|---|
| 5,071,970 | A | 12/1991 | le Grand et al. |
| 5,328,708 | A | 7/1994 | Rizzi et al. |
| 6,086,910 | A | 7/2000 | Howard et al. |
| 6,409,996 | B1 | 6/2002 | Plaschke |
| 6,620,425 | B1 | 9/2003 | Gardiner |
| 7,833,560 | B2 | 11/2010 | Velissariou et al. |
| 2005/0147723 | A1 | 7/2005 | Liu |
| 2006/0105089 | A1 | 5/2006 | Chu et al. |
| 2006/0134306 | A1 | 6/2006 | Zelkha et al. |
| 2010/0331399 | A1 | 12/2010 | Wood et al. |

FOREIGN PATENT DOCUMENTS

| | | |
|---|---|---|
| JP | H10165139 A | 6/1998 |
| WO | 2012012844 A1 | 2/2012 |

OTHER PUBLICATIONS

Fellows "Food Processing Technology, Principles and Practice", (2nd edition), 2000, Chapter 6, pp. 140-161.

Arthey et al. "Fruit Processing", New York, 1996, pp. 210-219.

English translation of Office Action from Japanese Patent Application 2015-527742; dated Sep. 5, 2017; Kanda K.

Giacomo, G. et al. "A new high-yield process for the industrial production of carrot juice", Food Bioprocess Technol, 2, 441-446 (2009).

Cieslik, E. et al. "Contents of polyphenols in fruit and vegetables", Food Chemistry, 94, 135-142 (2006).

GEA Mechanical Equipment. "Potato Starch Processing Custom-Fit Solutions from GEA." Document B_RR-13-04-0003 EN. Apr. 2013.

Bergthaller, W. Chemical and functional properties of food saccharides. Chapter 8. "Starch World Markets and Isolation of Starch," Ed. Piotr Tomasik. CRC Press, Boca Raton, London, New York, Washington D.C., 2004, 103-123.

Perez-Jimenez, J. et al. "Identification of the 100 richest dietary sources of polyphenols: an application of the Phenol-Explorer database", European Journal of Clinical Nutrition, 64, S112-S120 (2010).

SYSTEM AND PROCESS FOR EXTRACTION OF PRODUCTS FROM APPLE PEEL

CROSS-REFERENCE TO RELATED APPLICATIONS

This application is filed under 37 CFR 1.53(b) as a continuation application. This application claims priority under 35 U.S.C. § 120 from and the benefit of U.S. patent application Ser. No. 15/960,710, filed on Apr. 24, 2018, which is a Continuation application of U.S. patent application Ser. No. 14/422,712, filed on Feb. 20, 2015, which is a U.S. National Phase application under 35 U.S.C. § 371 of PCT/CA2013/000726, filed Aug. 16, 2013, which claims priority from and the benefit of U.S. provisional patent application No. 61/691,049, filed Aug. 20, 2012, the specifications of which are hereby incorporated by reference in their entireties.

BACKGROUND

(a) Field

The subject matter disclosed generally relates to a system and processes for extraction of at least one product from a source of fruit or vegetable matter. More specifically, the subject matter disclosed generally relates to a system and processes using a counter-current wash process, whereby the liquid extract containing the at least one product is further filtered and concentrated.

(b) Related Prior Art

Fruit or vegetable matter can be extracted by various processes in order to obtain a multitude of useful products, such as fibers, sugars, and phytochemical compounds. Among these phytochemicals compounds, polyphenols are recognized for their numerous biological properties, such as antibacterial/antiviral properties, vasodilatation properties, anticarcinogenic properties, anti-inflammatory properties, antioxidant properties, etc. Therefore, their extraction from fruits or vegetables for obtaining concentrated extracts which may be included into other products is highly desirable.

The use of enzymes and solvents such as ethanol or methanol can improve polyphenol recovery during extraction from fruit or vegetable matter. This is based on the fact that using ethanol or methanol as a solvent can lead to significantly more extraction yield than using water because the solubility of some products, such as polyphenols is higher in ethanol and methanol (Sluis, et al. 2001, Virot, et al. 2010). Even though the solubility in water is less, it is possible to reach the same overall level of extraction with water by applying several successive wash steps on the fresh biomass. Moreover, ethanol and methanol solvents are expensive and require additional steps to eliminate them from the final products, which increase the total cost of using a process which uses them. Also, enzyme treatment may cause irreversible damages to some of the products which can be extracted from such fruit or vegetable matter. For example, enzymatic treatment using pectinase may damage pectin from fruits and vegetables during the extraction process. Therefore, no enzymatic treatment is desired in order to keep the pectin intact through a system and process for extraction of products from fruits and vegetables.

Therefore, there is a need for a system and a process that does not use enzymatic pre-treatment.

Also, therefore, there is a need for a system and a process that use water as a solvent.

The process of the present invention is based on successive washes using water as a solvent. For that matter, a multiple steps counter-current wash process has been developed.

SUMMARY

According to an embodiment, there is provided a system for extraction of at least one product from a source of fruit or vegetable matter in a solvent comprising:
  a separator, for extracting the at least one product from the source of fruit or vegetable matter in a solvent comprising
    at least a first separator centrifuge comprising
      a first separator centrifuge entry for receiving the source of fruit or vegetable matter in a solvent,
      a first separator centrifuge exit, and
      an extract exit for receiving a first wash from the first separator centrifuge;
    a solvent inlet, for introducing the solvent in the separator,
  an ultrafiltration unit in fluid communication with the extract exit and comprising a filter, a retentate exit, and a permeate exit.

The system may further comprise a mixer having at least one mixing tank for dissolving and decanting the source of fruit or vegetable matter in a solvent.

The separator may further comprise a second separator centrifuge comprising:
  a second separator centrifuge entry in fluid communication with the first separator centrifuge exit,
  a second separator centrifuge exit, and
  a first counter-current supply in fluid communication with the mixer and/or the first separator centrifuge, for introducing counter-currently a second wash from the second separator centrifuge in the mixer and/or the first separator centrifuge.

The separator may further comprise a third separator centrifuge comprising:
  a third separator centrifuge entry in fluid communication with the second separator centrifuge exit,
  a third separator centrifuge exit, and
  a second counter-current supply in fluid communication with the second separator centrifuge for introducing counter-currently a third wash from the third separator centrifuge in the second separator centrifuge.

The solvent inlet may be in fluid communication with the third separator centrifuge.

According to another embodiment, there is provided a system for extraction of at least one product from a source of fruit or vegetable matter comprising:
  a mixer comprising
    at least one mixing tank for dissolving and decanting the source of fruit or vegetable matter in a solvent;
  a separator comprising
    a first, second and third separator centrifuge, for extracting the at least one product from the source of fruit or vegetable matter dissolved in the solvent,
    the first separator centrifuge comprising
      a first separator centrifuge entry in fluid communication with the mixer for receiving the source of fruit or vegetable matter dissolved in the solvent,
      a first separator centrifuge exit, and
      an extract exit for receiving a first wash from the first separator centrifuge;

the second separator centrifuge comprising
  a second separator centrifuge entry in fluid communication with the first separator centrifuge exit,
  a second separator centrifuge exit, and
  a first counter-current supply in fluid communication with the mixer for introducing counter-currently a second wash from the second separator centrifuge in the mixer;
the third separator centrifuge comprising
  a third separator centrifuge entry in fluid communication with the second separator centrifuge exit,
  a third separator centrifuge exit, and
  a second counter-current supply in fluid communication with the second separator centrifuge for introducing counter-currently a third wash from the third separator centrifuge in the second separator centrifuge; and
a solvent inlet, for introducing the solvent in the third the third separator centrifuge.

The system may further comprise a feed pump between the mixer and the first separator centrifuge entry, for pumping the source of fruit or vegetable matter in the solvent.

The system may further comprise a pre-filter connected between the pump and the first separator centrifuge entry.

The system may further comprise a fiber collector, for collecting a fiber from the source of fruit or vegetable matter, the fiber collector being connected to the third separator centrifuge exit and comprising at least one fiber collector entry and a fiber collector exit.

The system may further comprise a fiber collector pump, for pumping the fiber into a dryer.

The system dryer may be a spray dryer.

The system may further comprise an ultrafiltration unit in fluid communication with the extract exit and comprising a filter, a retentate exit, and a permeate exit.

The filter may have a 10 kDa cutoff, for passage of particles of size 10 kDa or smaller from the first wash.

The retentate exit may be in fluid communication with the at least one fiber collector entry, for collection of a retentate in the fiber collector.

The system may further comprise a concentrator unit, in fluid communication with the ultrafiltration unit, for concentration of a permeate obtained from the ultrafiltration unit into a concentrated permeate, the concentrator unit comprising a concentrator unit entry and a concentrator unit exit.

The concentrator unit may be a reverse osmosis unit.

The concentrator unit may be a vacuum evaporator unit.

The vacuum evaporator unit may further comprise a vent.

The concentrator unit may further comprise a vacuum evaporator unit.

The vacuum evaporator unit may further comprise a vent.

The system may further comprise a filter for filtration of the permeate, the filter comprising a filter entry in fluid communication with the ultrafiltration unit exit, a first filter exit and a filter second exit.

The system may further comprise a filter for filtration of the concentrated permeate, the filter comprising a filter entry in fluid communication with the concentrator unit exit, and a filter exit.

The filter may comprise a filtration resin.

The resin may be a macroreticular aromatic polymer matrix resin.

The system may further comprise an extract receiver for receiving a final extract, the extract receiver comprising an extract receiver entry in fluid communication with the filter exit, and an extract receiver exit.

The system may further comprise an extract receiver pump, for pumping the final extract.

The system comprise a concentrator unit, in fluid communication with the final filter, for concentration of a sugar fraction obtained from the final filter, the concentrator unit comprising a concentrator unit entry and a concentrator unit exit.

The concentrator unit may be a reverse osmosis unit.

The concentrator unit may be a vacuum evaporator unit.

The vacuum evaporator unit may further comprise a vent.

The concentrator unit may further comprise a vacuum evaporator unit.

The vacuum evaporator unit may further comprise a vent.

The system may further comprise a drier, in fluid communication with the final filter, for drying of a final extract obtained from the final filter and obtain a dried final extract.

The drier may comprise a spray drier, having a spray drier first entry in fluid communication with the final filter, and a spray drier second entry, a spray drier first exit for collection of a dried final extract from the spray drier, and a spray drier second exit.

The drier may further comprise a cyclonic separator for collection of a final particle of the dried final extract from the spray drier, having a cyclonic separator entry in fluid communication with the spray drier second exit, a cyclonic separator first exit for collection of the final particle of the dried final extract from the cyclonic separator, and a cyclonic separator second exit.

The drier may further comprises a condenser unit for condensing a solvent from the final extract, having a condenser unit entry in fluid communication with the cyclonic separator second exit, a condenser unit exit for collection of the solvent and of a gas.

The condenser unit exit may be in fluid communication with the spray drier second entry, for recycling of the gas in the spray drier.

According to another embodiment, there is provided a process for extraction of at least one product from a source of fruit or vegetable matter comprising the step of:
  ultrafiltering a first wash with an ultrafiltration unit for obtaining a permeate, and a retentate,
  the first wash being extracted from a source of fruit or vegetable matter in a solvent in a separator comprising at least a first separator centrifuge.

The separator may further comprise a second separator centrifuge, in fluid communication with the first separator centrifuge, and the source of fruit or vegetable matter in a solvent moving in a flow direction from the first to the second separator centrifuge, wherein a second wash from the second separator centrifuge may be introduced counter-currently prior to or into the first separator centrifuge, for further extraction in the first separator centrifuge.

The separator may further comprise a third separator centrifuge, in fluid communication with the second separator centrifuge, and the source of fruit or vegetable matter in a solvent moving in a flow direction from the second to the third separator centrifuge, wherein a third wash from the third separator centrifuge may be introduced counter-currently into the second separator centrifuge, for further extraction in the second separator centrifuge.

The fiber of the source of fruit or vegetable matter may be obtained from the separator.

The process may further comprise the step of reintroducing solvent in the first separator centrifuge, for further extraction in the first separator centrifuge.

The solvent may be introduced into the separator.

According to another embodiment, there is provided a process for extraction of at least one product from a source of fruit or vegetable matter comprising the step of:
  i) extracting a source of fruit or vegetable matter in a solvent in a separator comprising a first, second and third separator centrifuge, the first separator centrifuge being in fluid communication with the second separator centrifuge, and the second separator centrifuge being in fluid communication with the third separator centrifuge,
    the source of fruit or vegetable matter in a solvent moving in a flow direction from the first to the second separator centrifuge, and from the second to the third separator centrifuge,
    for obtaining a first wash from the first separator centrifuge, and a fiber of the source of fruit or vegetable matter from the third separator centrifuge,
wherein
    a second wash from the second separator centrifuge may be introduced counter-currently prior to or into the first separator centrifuge, for further extraction in the first separator centrifuge;
    a third wash from the third separator centrifuge may be introduced counter-currently into the second separator centrifuge, for further extraction in the second separator centrifuge; and
the solvent may be introduced counter-currently into the third separator centrifuge.

The solvent may comprise an alcohol, water, or combinations thereof.

The solvent may be water.

The source of fruit or vegetable matter may be dried apple peel powder.

The source of fruit or vegetable matter may be fresh apple peel.

In the process of the present invention, any one of the first, second or third separator centrifuge may be a horizontal decanter centrifuge.

In the process of the present invention, any one of the first, second or third separator centrifuge may be a nozzle centrifuge.

The nozzle size of the nozzle centrifuge may be from about 0.6 mm to about 0.8 mm.

The concentration of a solid in a centrate may be from about 10% to about 30% of insoluble solid on a dry weight basis.

The concentration of a solid in a centrate may be less than about 1% volume.

The concentration of a solid in a centrate may be less than about 0.5% volume.

The concentration of a solid in a centrate may be less than about 0.1% volume.

The fold concentration of the first wash compared to the source of fruit or vegetable matter in a solvent may be from about 6-fold concentration to about 10-fold concentration.

The process according to the present invention may further comprise the step i'), prior to step i):
  i') suspending the source of fruit or vegetable matter in the solvent.

The suspending may comprise agitation of the source of fruit or vegetable matter and the solvent.

The process may further comprise recirculating the source of fruit or vegetable matter and the solvent for shearing the source of fruit or vegetable matter and maximizing extraction.

The solvent may be taken from the second wash.

The process may further comprise the step of drying the fiber of the source of fruit or vegetable matter, for obtaining a dried fiber.

The process may further comprise the step of:
  ii) filtering the first wash with an tangential flow filter unit for obtaining a permeate, and a retentate.

The tangential flow filter unit may comprise a tangential flow membrane.

The tangential flow membrane may comprise an ultrafiltration membrane having a 10 kDa cutoff, for passage of particles of size 10 kDa or smaller from the first wash, for obtaining the permeate.

The tangential flow membrane may be an inert spiral or hollow fiber membrane.

The tangential flow membrane may be a polysulfone spiral membrane.

The process may further comprise the step of washing the retentate, for recovering a soluble retentate fraction and pectin.

The process may further comprise drying the retentate, for obtaining a dried retentate.

The process may further comprise combining and drying the retentate with the fiber of the source of fruit or vegetable matter, for obtaining a dried retentate and fiber combination.

The process may further comprise the step of:
  iii) concentrating the permeate with a concentrator unit, for obtaining a concentrated permeate.

The concentrator unit may comprise a reverse osmosis unit.

The reverse osmosis unit may comprise a reverse osmosis membrane.

The concentrator unit may comprise a vacuum evaporator unit.

The concentrator unit may further comprise a vacuum evaporator unit.

The vacuum evaporator unit may operate at a temperature from about 40° C. to about 45° C.

The tangential flow filter may comprise an ultrafiltration membrane, and the concentrator unit comprises a reverse osmosis unit and a vacuum evaporator unit.

The process may further comprising the step of drying the concentrated permeate with a carrier, for obtaining a dried concentrated permeate.

The carrier may be chosen from a food product having a glass transition temperature higher than a drying temperature of the concentrated permeate.

The carrier may comprise a maltodextrin.

The process may further comprise the step of:
  iii) filtering the permeate with a final filter, for obtaining a final extract and a sugar fraction.

The process may further comprise the step of:
  iv) filtering the concentrated permeate with a final filter, for obtaining a final extract and a sugar fraction.

The final filter may comprise a filtration resin.

The filtration resin may be a macroreticular aromatic polymer matrix resin.

The final extract may be eluted from the filtration resin with a solution chosen from ethanol, or an alkaline aqueous solution.

The filtration resin may be washed with water.

The filtration resin may be washed once, twice, or three times.

The filtration resin may be washed with agitation.

The final filter may comprise the filtration resin in a batch container.

The final filter may comprises the filtration resin in a flow cartridge.

The final filter may comprise the filtration resin in a flow cartridge comprising a flow diversion valve to reintroduce a water wash in the flow cartridge.

The process may further comprise the step of drying the final extract with a carrier, for obtaining a dried final extract.

The carrier may be chosen from a food product having a glass transition temperature higher than a drying temperature of the concentrated permeate.

The carrier may comprise a maltodextrin.

The process may further comprise the step of:
iv) concentrating the sugar fraction with a concentrator unit, for obtaining a concentrated sugar fraction.

The concentrator unit may comprise a reverse osmosis unit.

The reverse osmosis unit may comprise a reverse osmosis membrane.

The concentrator unit may comprise a vacuum evaporator unit.

The concentrator unit may further comprise a vacuum evaporator unit.

The vacuum evaporator unit may operate at a temperature from about 40° C. to about 45° C.

The process may further comprise the step of:
v) drying the final extract with a drier, for obtaining a dried final extract.

The process may be a continuous process.

According to another embodiment, there is provided a concentrated permeate produced by the process according to the present invention.

The concentrated permeate may have a concentration from about 13.5% Brix to about 60% Brix.

The concentrated permeate may have a concentration from about 50% Brix to about 60% Brix.

According to another embodiment, there is provided a concentrated permeate produced by the process according to the present invention.

The concentrated permeate may have a concentration from about 20% Brix to about 25% Brix.

According to another embodiment, there is provided a dried concentrated permeate produced by the process of the present invention.

According to another embodiment, there is provided a final extract produced by the process according to any one of claims 81 to 90.

The final extract may have a concentration of up to about 85% in polyphenols.

According to another embodiment, there is provided a dried final extract produced by the process according to the present invention.

The dried final extract may have a concentration of up to about 85% in polyphenols.

According to another embodiment, there is provided a sugar fraction produced by the process of the present invention.

According to another embodiment, there is provided a concentrated sugar fraction produced by the process according to the present invention.

According to another embodiment, there is provided a sugar fraction produced by the process according to the present invention.

The sugar fraction may be eluted from the final filter with the water.

The sugar fraction may have a concentration of about 95% fructose DWB, and about 5% sucrose DWB.

According to another embodiment, there is provided a fiber of the source of fruit or vegetable matter produced by the process according to the present invention.

According to another embodiment, there is provided a dried fiber produced by the process of the present invention.

According to another embodiment, there is provided a dried retentate produced by the process of the present invention.

According to another embodiment, there is provided a dried retentate and fiber combination produced by the process of the present invention.

The dried retentate may comprise pectin.

According to another embodiment, there is provided a composition comprising at least two of
a concentrated permeate according to the present invention;
a dried concentrated permeate according to the present invention;
a final extract according to the present invention;
a dried final extract according to the present invention;
a sugar fraction according to the present invention;
a concentrated sugar fraction according to the present invention;
a fiber according to the present invention;
a dried fiber according to the present invention; and
a dried retentate according to the present invention.

The following terms are defined below.

The term "polyphenol" is intended to mean molecules that contain multiple phenol groups (benzene ring with a hydroxide connection). Phenols have antioxidant properties, which means they can neutralize oxidizing molecules that would otherwise damage human cells. Polyphenols are amphipathic molecules, with "hydrophobic" rings and "hydrophilic", weak-acid, hydroxyl groups (pKa between 9 and 10). Polyphenol compounds include without limitations flavonols (e.g. quercetin, 3-hydroxyphloretin 2'-xylglucoside, 3-hydroxyphloretin 2'-glucoside, Phloretin 2'-xylglucoside, Phloridzin, 3,5,7,3'14'-pentahydroxy-flavonol-3-O-β-D-galactopyranoside, 3,5,7,3'14'-pentahydroxy-flavonol-3-O-β-D-glucopyranoside, 3,5,7,3'14'-pentahydroxy-flavonol-3-O-α-L-arabinofuranoside, (–)-catechin, (–)-epicatechin, Cyanidin 3-galactoside, Quercetin 3-galatoside, Quercetin 3-glucoside, Quercetin 3-xyloside, Quercetin 3-arabinoside, Quercetin 3-rhamnoside), procyanidins (e.g. catechins, procyanidin B1, procyanidin B2), Hydroxycinnamic acids (e.g. chlorogenic acid, P-coumaroxyquinic acid), and Dihydrochalcone (e.g. phlorizin, 3-hydroxyphloretin 2'-xylglucoside, 3-hydroxyphloretin 2'-glucoside, Phloretin 2'-xylglucoside, Phloridzin).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
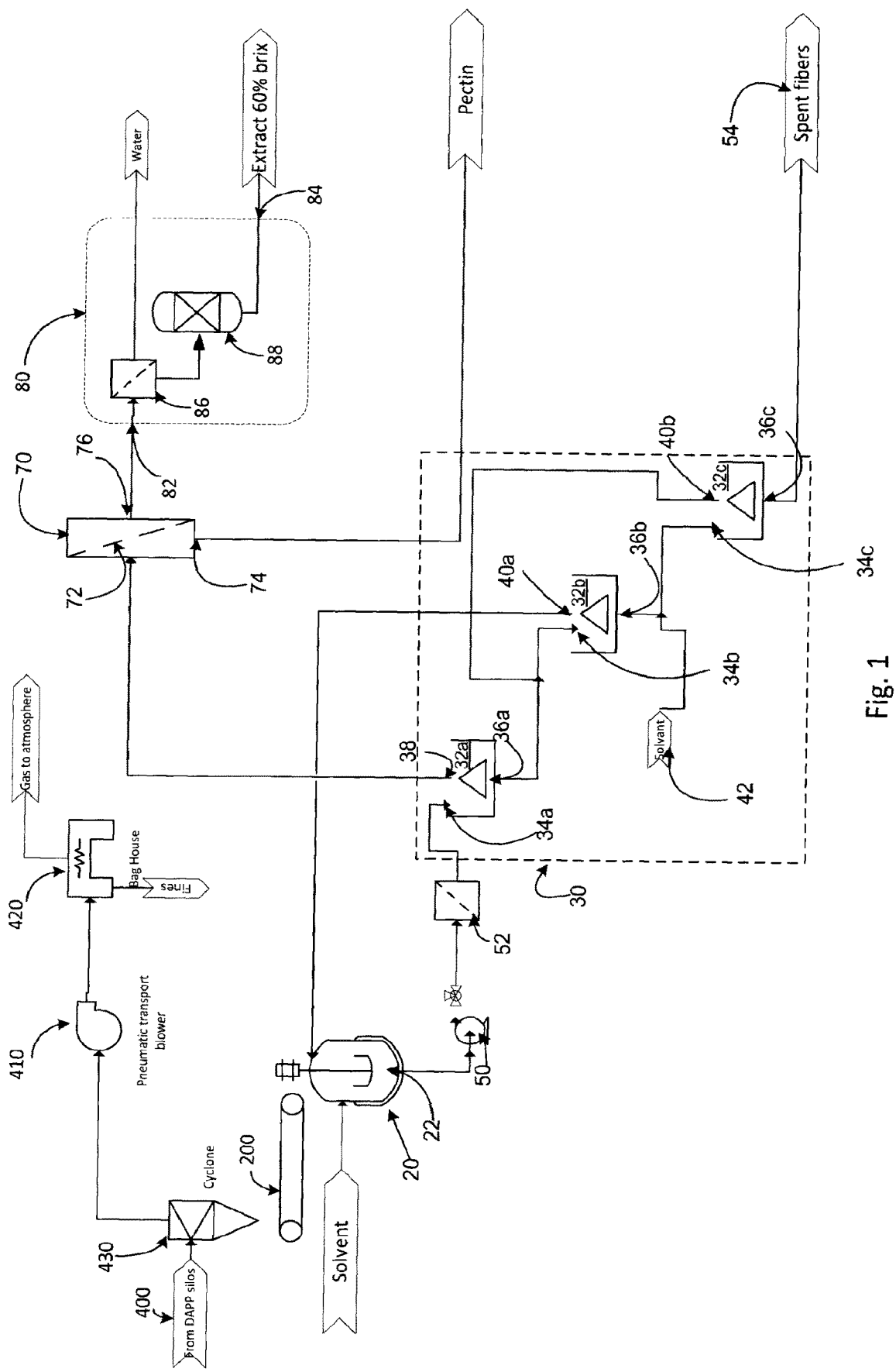
FIG. 1 illustrates a flow diagram of a system according to an embodiment of the present invention.

In embodiments there are disclosed system and processes for extraction of at least one product from a source of fruit or vegetable matter.

Basic Description

According to embodiment, the system and process considered in the present invention are based on successive washes using water as a solvent. The system and processes investigated do not use enzymatic pre-treatment (Pinelo, Zornoza et S. Meyer 2008). Preferably, they do not also use other polar solvent (POS Bio-Sciences 2011, B. B. Li, B. Smith et Md. M. Hossain 2006). Using polar solvents such as ethanol or methanol can lead to significantly more extraction yield than using water because the solubility of some polyphenols is higher in ethanol and methanol (Sluis, et al. 2001, Virot, et al. 2010). Even though it is demonstrated the use of enzymes and ethanol/methanol can improve polyphenol recovery during extraction, the system and processes of the present invention preferably use water for polyphenol extraction. The use of enzyme is not considered in this application as it degrades the pectin. Keeping the pectin intact in the system and/or through the processes of the present invention may be important, as it is a valuable product that may be resold. Even though the solubility in water is less, it is possible to reach the same overall level of extraction with water by applying several successive wash steps on the fresh biomass. Therefore, a multiple steps counter-current wash process is used to achieve the desired purification. The system and process may be used or carried out in batch mode, or in a continuous manner.

System

Referring now to the drawings, and more particularly to FIGS. 1 to 4, flow diagrams which illustrates systems according to embodiments of the present invention. The system 10 is for extraction of at least one product from a source of fruit or vegetable matter. According to an embodiment, the system a separator 30, for extracting the at least one product from the source of fruit or vegetable matter in a solvent, which comprises at least a first separator centrifuge 32a (FIGS. 2 and 4) comprising a first separator centrifuge entry 34a for receiving the source of fruit or vegetable matter in a solvent, a first separator centrifuge exit 36a, and an extract exit 38 for receiving a first wash from said first separator centrifuge. The separator 30 also comprises a solvent inlet 42, for introducing the solvent in the separator 30. The system also includes an ultrafiltration unit 70 in fluid communication with the extract exit 38 and comprising a filter 72, a retentate exit 74, and a permeate exit 76.

According to another embodiment, the system comprises a mixer 20 including at least one mixing tank 22 for dissolving and decanting the source of fruit or vegetable matter in a solvent.

The source of fruit or vegetable matter may be carried to the extraction plant for example by pneumatic transport 410 from the storage 400 (and attendant cyclonic separator 430). The pneumatic transport 410 is preferred over conveyors as it is flexible and can be easily installed for the considered flows of source of fruit or vegetable matter. The source of fruit or vegetable matter may then be deposited on conveyor 200, for continuous introduction into mixer 20.

According to another embodiment, the system 10 may include a separator 30 which further includes a second separator centrifuge 32b having a second separator centrifuge entry 34b in fluid communication with the first separator centrifuge exit 36a, a second separator centrifuge exit 36b, and a first counter-current supply 40a in fluid communication with the mixer 20 and/or the first separator centrifuge 32a for introducing counter-currently a second wash from the second separator centrifuge 32b in the mixer 20 and/or the first separator centrifuge 32a.

According to yet another embodiment (FIGS. 2 and 4), the system 10 may include a separator 30 which further includes a third separator centrifuge 32c having a third separator centrifuge entry 34c in fluid communication with the second separator centrifuge exit 36b, a third separator centrifuge exit 36c, and a second counter-current supply 40b in fluid communication with the second separator centrifuge for introducing counter-currently a third wash from the third separator centrifuge in the second separator centrifuge.

According to an embodiment, the solvent inlet 42 may be in fluid communication with the third separator centrifuge 32c.

According to another embodiment (See FIGS. 2 and 4), the system 10 may include a separator 30 which includes a first, second and third separator centrifuge (32a, 32b, 32c, respectively), for extracting the at least one product from the source of fruit or vegetable matter dissolved in the solvent. The first separator centrifuge 32a comprises a first separator centrifuge entry 34a, in fluid communication with the mixer 20 for receiving the source of fruit or vegetable matter dissolved in the solvent, a first separator centrifuge exit 36a, and an extract exit 38 for receiving a first wash from the first separator centrifuge. The second separator centrifuge 32b comprises a second separator centrifuge entry 34b in fluid communication with the first separator centrifuge exit 36a, a second separator centrifuge exit 36b, and a first counter-current supply 40a in fluid communication with the mixer 20 for introducing counter-currently a second wash from the second separator centrifuge 32b in the mixer 20. The third separator centrifuge 32c comprises third separator centrifuge entry 34c in fluid communication with the second separator centrifuge exit 36b, a third separator centrifuge exit 36c, and a second counter-current supply 40b in fluid communication with the second separator centrifuge, for introducing counter-currently a third wash from the third separator centrifuge 32c in the second separator centrifuge 32b. A solvent inlet 42, is also present for introducing the solvent in the third said third separator centrifuge 32c.

According to an embodiment, the system 10 may further include a feed pump 50, located between the mixer 20 and the first separator centrifuge entry 34a. The pump 50 may be used for pumping the source of fruit or vegetable matter dissolved in the solvent. According to another embodiment, the system may further include a pre-filter 52, which is connected between the pump 50 and the first separator centrifuge entry 34a.

At the other end of the system connected to the third separator centrifuge exit 36c, may be a fiber collector 54, for collecting a fiber from the source of fruit or vegetable matter. The fiber collector 54 comprises at least one fiber collector entry 56 and a fiber collector exit 58. The fiber collector 54 may also be accompanied by a fiber collector pump 60, for pumping fiber into an attendant dryer, for example a spray dryer.

According to another embodiment, the system further includes an ultrafiltration unit 70, in fluid communication with the extract exit 38 and comprising a filter 72, a retentate exit 74, and a permeate exit 76. According to a preferred embodiment, the filter 72 has a 10 kDa cutoff, which allows the passage of particles of size 10 kDa or smaller from the first wash. The retentate exit 74 may be in fluid communication with the at least one fiber collector entry 56, for collection of a retentate in the fiber collector 54.

According to another embodiment, the system may further comprise a concentrator unit 80, in fluid communication with the ultrafiltration unit 70, for concentration of a permeate obtained from the ultrafiltration unit 70 into a concentrated permeate. The concentrator unit 80 may include a concentrator unit entry 82 and a concentrator unit exit 84. According to some embodiments, the concentrator unit 80 may be a reverse osmosis unit 86 or a vacuum evaporator unit 88, or combinations thereof (See FIGS. 1 and 3). The vacuum evaporator unit 88 may further comprise a vent. Water may be obtained from the reverse osmosis unit 86, and the evaporator unit may yield a concentrated permeate comprising up to a 60% Brix extract containing up to 15% polyphenol content.

According to another embodiment, the system may further comprise an extract receiver 100, for receiving an extract, such as the 60% Brix extract containing up to 15% polyphenol content. The extract receiver 100 includes an extract receiver entry 102 in fluid communication with said concentrator unit exit 84, and an extract receiver exit 104. The extract receiver 100 may also be connected to an extract receiver pump 106, for pumping the extract.

According to another embodiment, the system may comprise a filter 90 for filtration of the permeate, in fluid communication with the ultrafiltration unit 70. The filter 90 comprises a filter entry 92 in fluid communication with the permeate exit 76, a first filter exit 94 and a second filter exit 96. According to an embodiment, the filter 90 may comprise a filtration resin. The resin may be a macroreticular aromatic polymer matrix. Non limiting examples of suitable resins include Amberlite™ resins, such as the Amberlite™ FPX66 resin.

According to another embodiment, the system may further comprise a concentrator unit 80, in fluid communication with the filter 90, for example through second filter exit 96, for concentration of a permeate obtained from the filter 90 into a concentrated permeate. The concentrator unit 80 may include a concentrator unit entry 82 and a concentrator unit exit 84. According to some embodiments, the concentrator unit 80 may be a reverse osmosis unit 86 or a vacuum evaporator unit 88, or combinations thereof (See FIGS. 2 and 4). The vacuum evaporator unit 88 may further comprise a vent. Water may be obtained from the reverse osmosis unit 86, and the evaporator unit may yield a concentrated permeate comprising up to a 60% Brix extract containing no polyphenol content.

According to another embodiment, the system may further comprise a drier 110, in fluid communication with the filter 90, for example through first filter exit 94, for drying of a final extract obtained from the filter 90 through first exit 94. The drier dries the final extract containing the polyphenolic compounds, yielding a dried final extract of up to about 85% polyphenol. The drier unit may comprise, for example, spray drier 112, having a spray drier first entry 114 in fluid communication with first exit 94, and having an spray drier first exit 116. Spray drier 112 may also have a second exit 118, in fluid communication with a cyclonic separator 120, which collects fine particles of polyphenolic matter. Cyclonic separator 120 has a cyclonic separator entry 122, in fluid communication with spray drier second exit 118, and a spray drier first exit 124. The dried final extract may be collected from the spray drier first exit 116 and the cyclonic separator first exit 124, combined and sent into an extract receiver such as an extract receiver 100 as described above. The drier 110 may also comprise a condenser unit 130, which is in fluid communication with the cyclonic separator through respective cyclonic separator second exit 126 and condenser unit entry 132. The condenser unit condenses the remaining ethanol solvent, which may then be collected through condenser unit exit 134, while nitrogen used in the drying process is cycled back into the spray drier 112 through, for example, second entry 119.

Process—Design Basis

The process is based on 1,800,000 lbs/year of a source of fruit or vegetable matter (e.g. any suitable source of fruit or vegetable matter. Preferably, the source of fruit or vegetable matter is Dried Apple Peel Powder, DAPP). The source of fruit or vegetable matter may also be fresh apple peel. According to an embodiment, the DAPP produced is 10% from organic sources and the rest is non-organic. It is assumed that 50% of the organic DAPP and about 80% of the non-organic will be extracted. Preferably, the DAPP is from an organic source. Using organic apple peels eliminates the presence of pesticide in the DAPP. According to another embodiment of the present invention, when non-organic products are considered for extraction, abrasive methods for cleaning the vegetables and fruits should be considered to remove most of the pesticides prior to the extraction process. Otherwise, the final products, especially those obtained after extraction on a food grade extraction resin which also have affinities for pesticide compounds, will contain said pesticides mixed with the polyphenolic compounds, which is not desirable. The nominal DAPP feed to the process is then 41 tons/year of organic and 589 tons of non-organic powder. According to an embodiment, the hourly feed to the plant is about 350 kg/h of DAPP. An intrinsic process efficiency of 60% would give a design feed rate of 583 kg/h.

Figure 5:
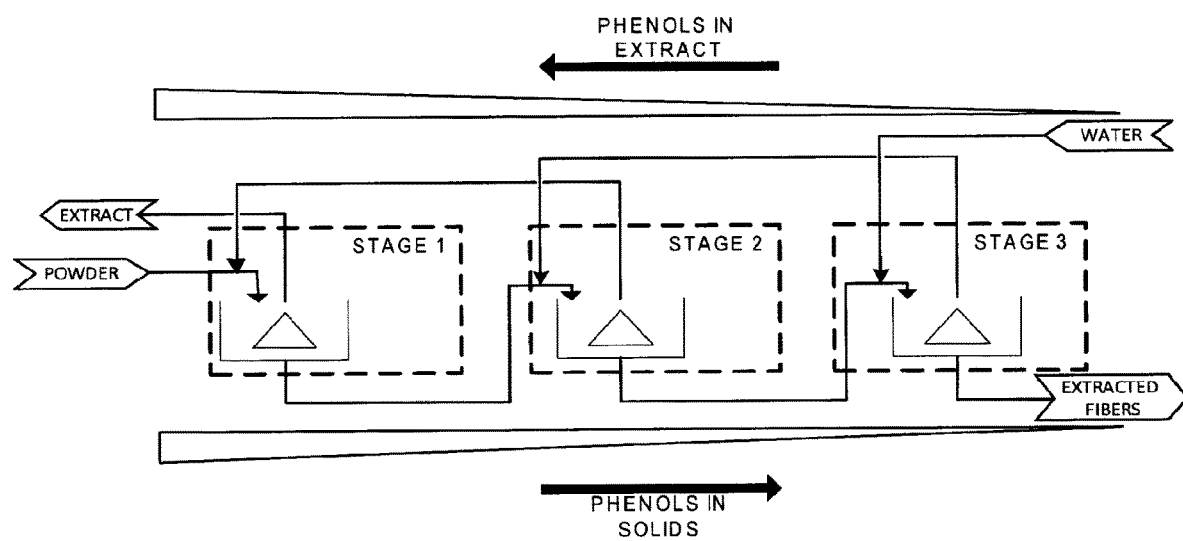
FIG. 5 illustrates the counter-current extraction rationale. The streams of high phenol concentrations are contacted together and the spent fibers are contacted with pure water to extract as much phenols as possible. It allows removing most of the phenols with a fraction of the water a co-current process would need. It also brings the extract concentration higher which reduces the costs of evaporation.

Therefore, according to another embodiment of the present invention, there is disclosed a process for extraction of at least one product from a source of fruit or vegetable matter. Now referring to FIG. 5.

According to an embodiment, the process comprises the step of ultrafiltering a first wash with an ultrafiltration unit (270) for obtaining a permeate, and a retentate. The first wash is extracted from a source of fruit or vegetable matter in a solvent in a separator 230 having at least a first separator centrifuge. Further solvent may be introduced into the first separator centrifuge 232a, for further extraction of the source of fruit or vegetable matter in the first separator centrifuge 232a, such that successive washes are obtained from the source of fruit or vegetable matter.

According to another embodiment, the separator 230 may further include a second separator centrifuge 232b, in fluid communication with the first separator centrifuge 232a, and the source of fruit or vegetable matter in a solvent is moving in a flow direction from the first to said second separator centrifuge (232a, 232b). A second wash from the second separator centrifuge 232b is introduced counter-currently prior to or into the first separator centrifuge 232a, for further extraction in the first separator centrifuge 232a.

According to another embodiment, the separator 230 may further include a third separator centrifuge 232c, in fluid communication with the second separator centrifuge, and the source of fruit or vegetable matter in a solvent is moving in a flow direction from the second to third separator centrifuge (232b, 232c). A third wash from the third separator centrifuge 232c is introduced counter-currently into the second separator centrifuge 232b, for further extraction in the second separator centrifuge 232b.

According to another embodiment, a fiber of the source of fruit or vegetable matter may be obtained from the separator 230. According to an embodiment, the solvent may be introduced into the separator 230. According to another embodiment, fresh solvent may be reintroduced in the first separator centrifuge 232a, for further extraction in the first separator centrifuge 232a. Also, solvent may be reintroduced countercurrently from the second separator centrifuge 232b in the first separator centrifuge 232a, for further extraction in the first separator centrifuge 232a.

According to another embodiment, the process may comprised the step of extracting a source of fruit or vegetable matter in a solvent in a separator 230 comprising a first, second and third separator centrifuge (232a, 232b, and 232c, respectively). The source of fruit or vegetable matter in a solvent is moving in a flow direction from the first to the second separator centrifuge (232a, 232b), and from the second to the third separator centrifuge (232b, 232c). From the process of the present invention is obtained a first wash, from the first separator centrifuge 232a, and a fiber of the source of fruit or vegetable matter from the third separator centrifuge 232c. During the extraction process, a second wash from the second separator centrifuge is introduced counter-currently prior to or into the first separator centrifuge, for further extraction in the first separator centrifuge 232a; a third wash from the third separator centrifuge 232c is introduced counter-currently into the second separator centrifuge 232b, for further extraction in the second separator centrifuge 232b; and the solvent is introduced counter-currently into the third separator centrifuge 232c. According to one embodiment, the first, second or third separator centrifuges (232a, 232b, and 232c, respectively) are horizontal decanter centrifuges. According to another embodiment, the first, second or third separator centrifuges (232a, 232b, and 232c, respectively) are nozzle centrifuge. According to some embodiments, the nozzle size of the nozzle centrifuges may be from about 0.6 mm to about 0.8 mm.

According to an embodiment, the concentration of solid in the centrate may be from about 10% to about 30% of insoluble solid on a dry weight basis. According to an embodiment, the concentration of solid in the centrate may be less than about 1% volume, or less than about 0.5% volume, or less than about 0.1% volume. According to another embodiment, the fold concentration of the first wash compared to the source of fruit or vegetable matter in a solvent may be from about 6-fold concentration to about 10-fold concentration.

According to another embodiment of the present invention, the process may further include the step of drying the fiber of the source of fruit or vegetable matter for obtaining a dried fiber.

According to embodiments of the present invention, the solvent may be an alcohol, water, or combinations thereof. Preferably, the solvent is water.

Hydration

According to another embodiment the process may further include the step i'), prior to step i) of suspending the source of fruit or vegetable matter in the solvent.

When the source of fruit or vegetable matter is DAPP, it is first carried to the extraction plant by pneumatic transport from the storage silos. The pneumatic transport is privileged over conveyors as it is flexible and can be easily installed for the considered flows. These systems are also simple to use and install and are relatively cheap.

According to another embodiment, when the source of fruit or vegetable matter is in a powder form, it has to be suspended in water to release the phenols embedded in the fibrous structure. According to pilot scale results (see below), when the source of fruit or vegetable matter is DAPP, the equilibrium is reached relatively fast when the DAPP is first suspended, meaning that there is very little mass transfer limitation between the solid structure of DAPP and the liquid phase.

The suspending and hydration step may take place for example in a stirred tank at room temperature (temperature ranging between 20-25° Celsius) and at natural pH of the solution (around 4.2-4.5). An initial 5-15 minutes agitation is enough to ensure proper dissolution of the solids in water. The suspending may comprise the agitation of the source of fruit or vegetable matter and the solvent. According to another embodiment, the process may further comprise recirculating the source of fruit or vegetable matter and the solvent for shearing the source of fruit or vegetable matter and maximizing extraction.

Figure 6:
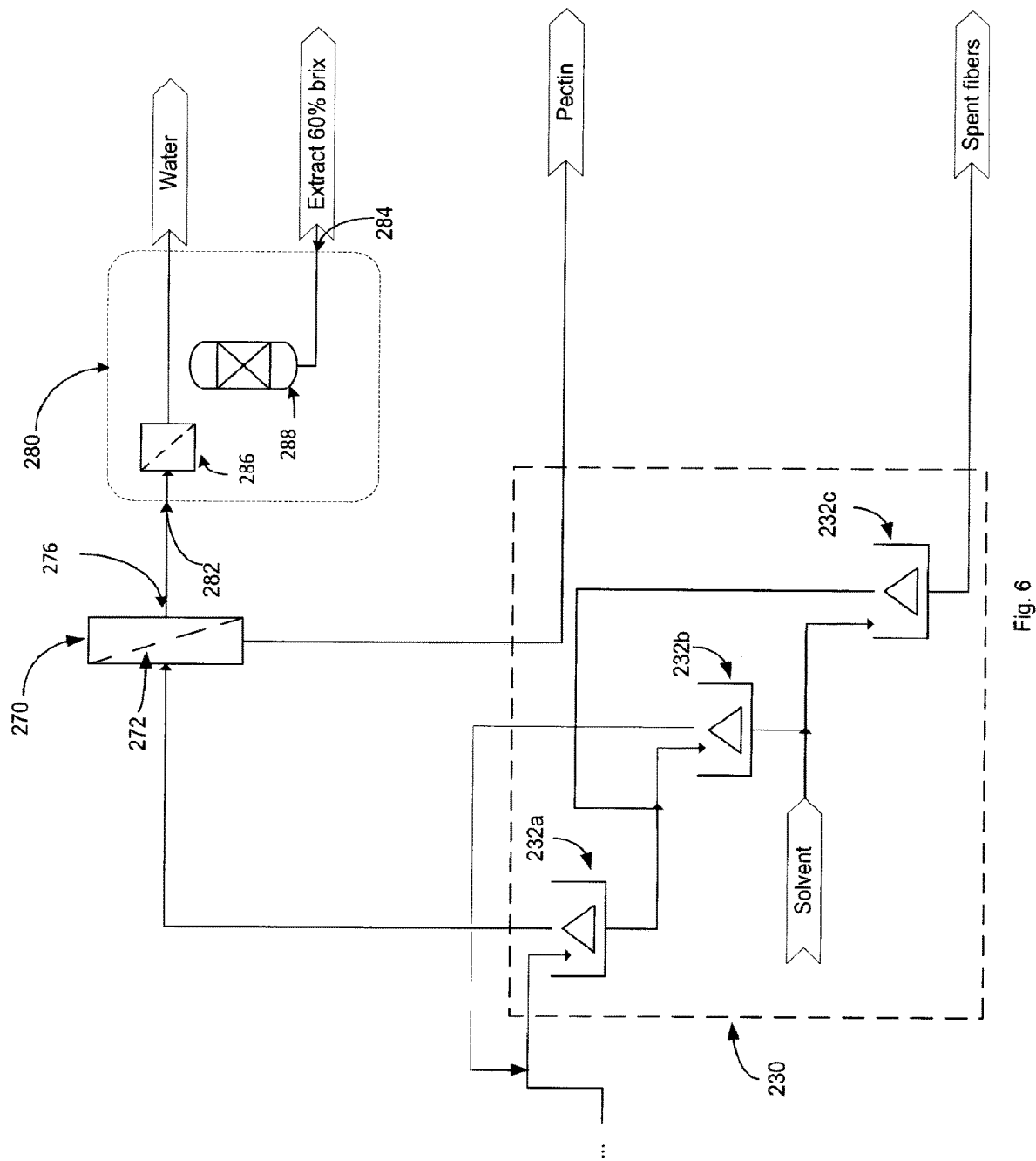
FIG. 6 illustrates a flow diagram of a process according to an embodiment of the present invention.

The hydration of the source of fruit or vegetable matter is made with the extract from previous washes, or with fresh water. According to an embodiment, there are several advantages of doing the extraction with water from previous washes:

a) Reduces the water make-up requirements of the process because the same water is back flowed from the back end of the process to the front end of the process (see FIG. 6).

b) Results in higher phenol concentration in the final extract because the extract successively contacts solids with increasing phenol concentration.

Figure 2:
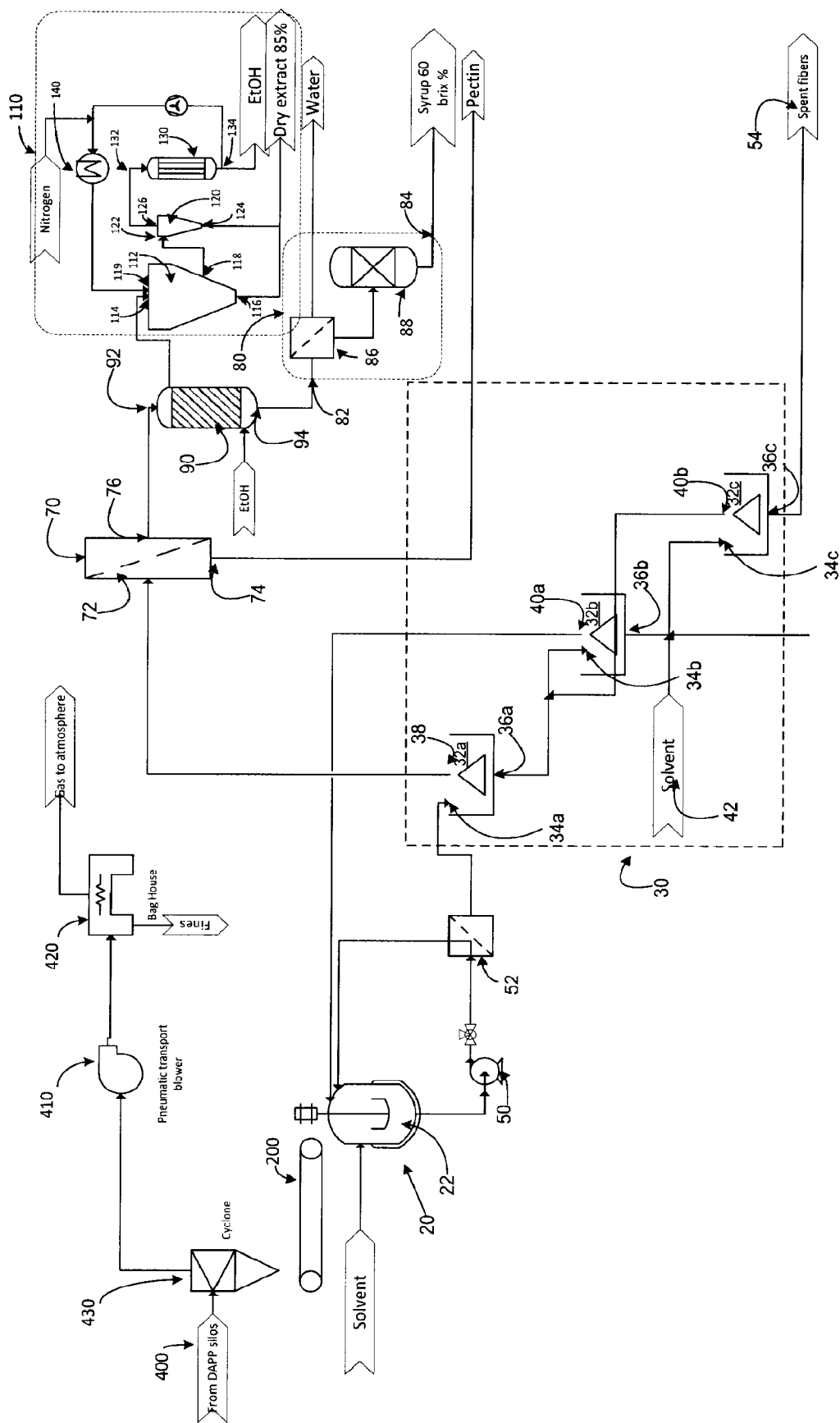
FIG. 2 illustrates a flow diagram of a process according to an embodiment of the present invention.
Figure 3:
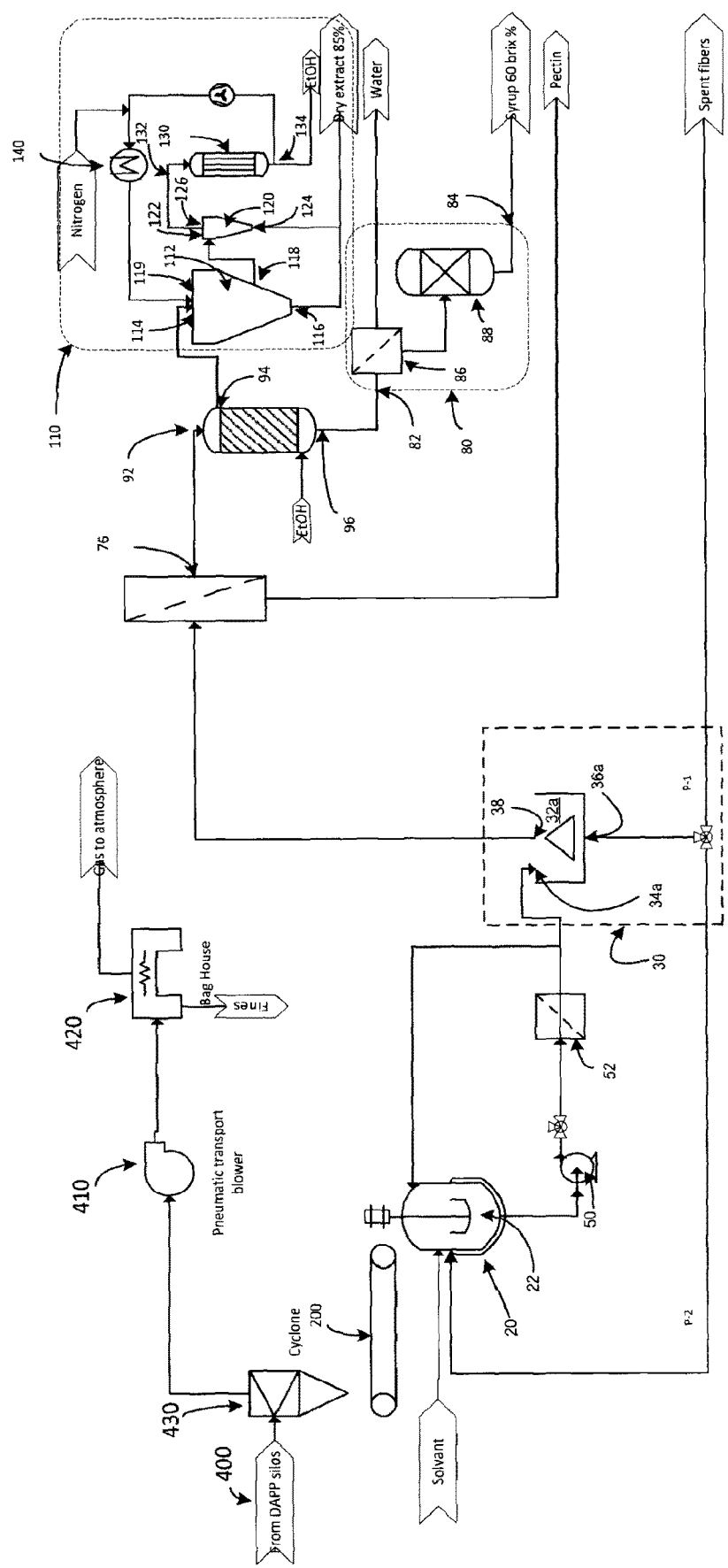
FIG. 3 illustrates a flow diagram of a process according to an embodiment of the present invention.
Figure 4:
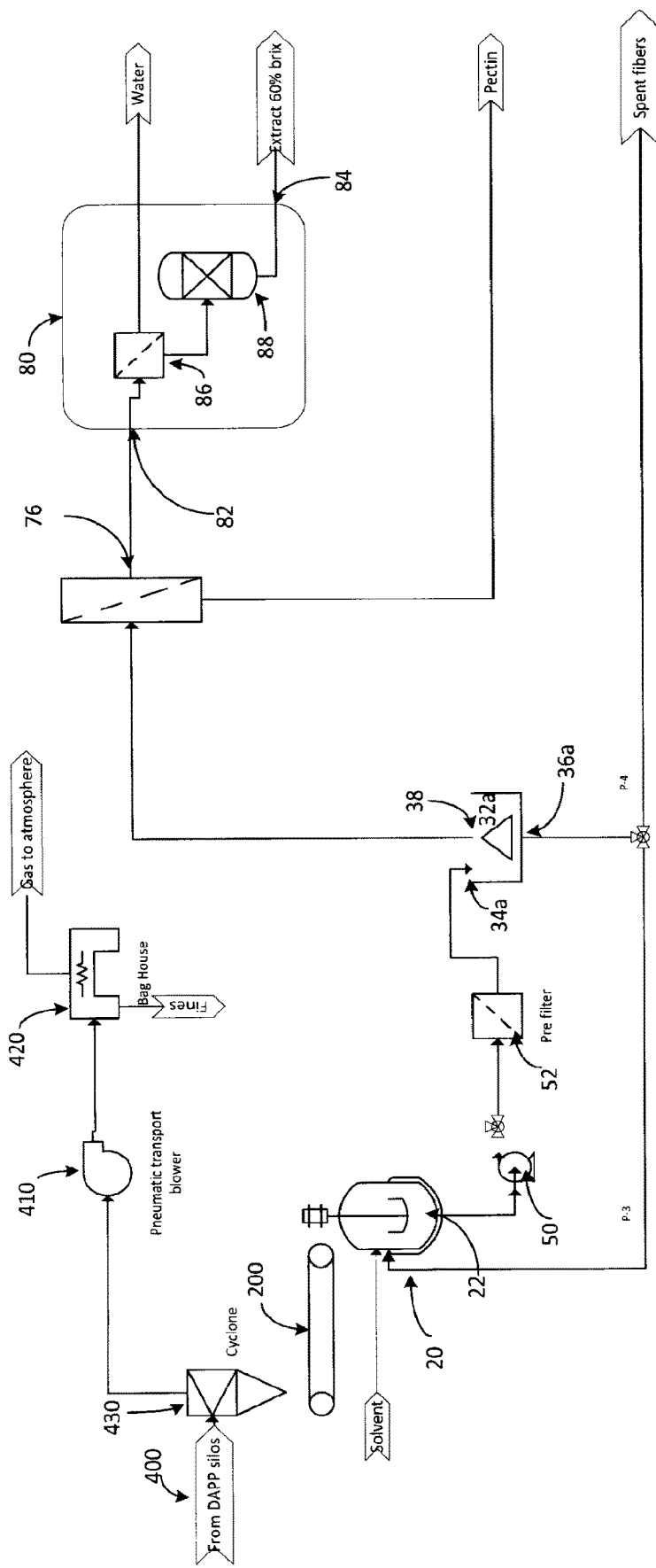
FIG. 4 illustrates a flow diagram of a process according to an embodiment of the present invention.

Therefore, according to an embodiment, and as shown in FIGS. 2 and 4, the solvent may be taken from the second wash.

According to another embodiment, the extraction may also be performed with fresh water. For example, the fresh water may be introduced during the hydration of the source of fruit or vegetable matter. According to another embodiment, when the source of water is fresh water used during the hydration of the source of fruit or vegetable matter, the extraction may be performed in a separator (30) having a first and second separator centrifuge (32a, 32b), with a second wash from the second separator centrifuge 32b being introduced counter-currently prior to or into the first separator centrifuge 32a, for further extraction in the first separator centrifuge 32a.

Ultrafiltering

The light phase (no insoluble solids) coming off the first separator centrifuge contains most of the water soluble compounds found in the DAPP and also contains a little fraction of non-soluble solids. These non-soluble solids, along with the pectin, are removed from the extract using an tangential flow filter unit 270 which comprises a tangential flow membrane, such as an ultrafiltration membrane having 10 kDa pore size. Larger pore membranes (e.g. 100 kDa pore size) would also be suitable, but are not preferred since the pectin would not be retained in the retentate. After removing most of the liquid out of the retentate, it is further washed with water during a diafiltration step to recover most of the soluble compounds present in the retentate.

Therefore, according to another embodiment, the process may further include the step of filtering the first wash with an tangential flow filter unit 270 for obtaining a permeate, and a retentate. The tangential flow filter unit 270 may comprise a tangential flow membrane, such as an ultrafiltration membrane 272, having a 10 kDa cutoff, for passage of particles of size 10 kDa or smaller from the first wash, for obtaining the permeate. According to some embodiments, the tangential flow membrane may be an inert spiral or hollow fiber membrane. According to another embodiment the tangential flow membrane may be a polysulfone spiral membrane.

According to another embodiment, the process may further comprise the step of washing the retentate for recovering a soluble retentate fraction and pectin. The retentate may further be dried, for obtaining a dried retentate. The process may also include, according to some embodiments, combining and drying the retentate with the fiber of the source of fruit or vegetable matter, for obtaining a dried retentate and fiber combination.

Concentration Process

According to an embodiment, after ultrafiltration, the extract needs to be concentrated as it mainly contains less than 1% dissolved solids. There are two approaches possible.

a) Vacuum evaporation: this process is a low temperature evaporation process which is validated up to 13.5% Brix during the pilot tests (see Example 1 below). The reason for stopping at 13.5% Brix is due to volume limitation, however it is believed it can easily reach 50-60% Brix. The temperature of operation of 40-45° C. may alter the product. Nevertheless, the product that comes out of this process is found to be satisfactory in terms of polyphenol concentration, flavor and color.

b) Reverse osmosis: this process is a low temperature membrane process which operates at high pressure (40-60 bars). The advantage is that it is a non-thermal process, thus may keep some key properties of the extract. Results obtained show that an upper limit of 20-25% Brix can be reached due to the osmotic pressure of the liquid. If a higher level of Brix is required, a small evaporator unit would be needed to reach the desired final Brix level. The size of this evaporator would be 25 times less than that of option a) in terms of capacity.

Therefore, according to some embodiments, the process may further include the step of concentrating the permeate with a concentrator unit 280, for obtaining a concentrated permeate. According to some embodiments, the concentrator unit 280 comprises a reverse osmosis unit, which comprises a reverse osmosis membrane. According to another embodiment, the concentrator unit 280 comprises a vacuum evaporator unit. According to another embodiment, the concentrator unit 280 comprises a reverse osmosis unit and a vacuum evaporator unit.

The vacuum evaporator unit may operate at temperatures from about 40 to about 45° C.

Purification Process

Purification is necessary should it be desired to increase the concentration of polyphenols in the extract on a dry weight basis (i.e. remove some sugars). The adsorption/desorption process using Dow Amberlite resins works very well and a final purity of 85% polyphenols on a dry weight basis can be reached in a single pass, where initial product was about 4.0% purity DWB. It is also possible with this process to increase the purity to various intermediate levels by processing only fractions of the feed to match the desired purity.

The use of resins for purification requires an eluting fluid to recover the purified extract. Ethanol has been used, but it is also possible to use an alkaline aqueous solution.

Therefore, according to an embodiment of the present invention, the process may be further comprising the step of filtering the concentrated permeate with a final filter 290, for obtaining a final extract and a sugar fraction. The final filter 290 may comprise a filtration resin. The resin may be a macroreticular aromatic polymer matrix. Non limiting examples of suitable resins include Amberlite™ resins, such as the Amberlite™ FPX66 resin.

Figure 7:
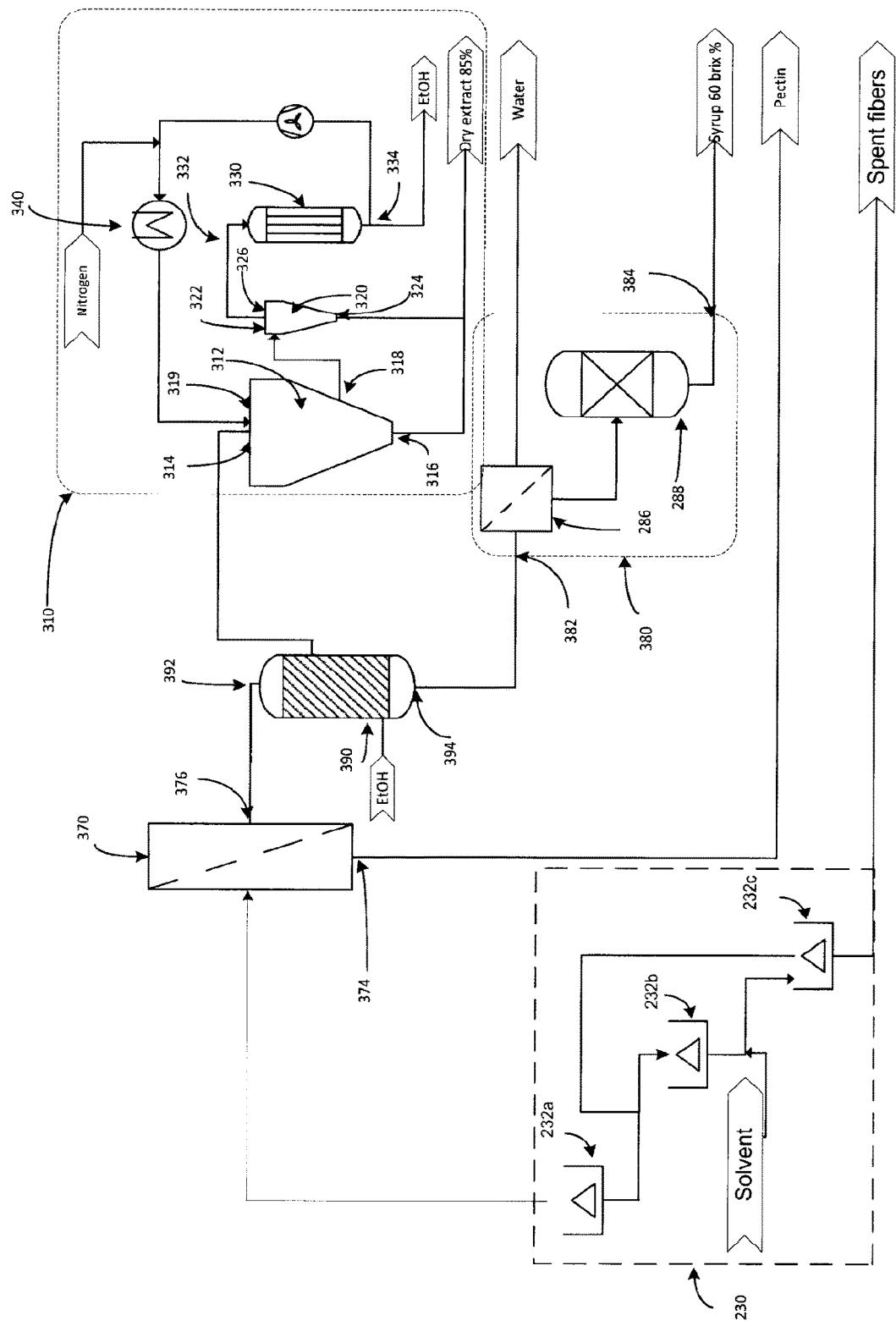
FIG. 7 illustrates a flow diagram of a process according to an embodiment of the present invention.

According to another embodiment of the present invention, the purification may also take place prior to concentration of the permeate off of the ultrafiltration unit. Now referring to FIG. 7. Therefore, according to an embodiment, the process may further comprise filtering the permeate with a final filter 390, for obtaining a final extract, and a sugar fraction. The final filter 390 may comprise a filtration resin. The resin may be a macroreticular aromatic polymer matrix. Non limiting examples of suitable resins include Amberlite™ resins, such as the Amberlite™ FPX66 resin.

According to either embodiment, the filtration resin may be washed with water, for example, once, twice, or three or more times. The resin may be washed with agitation. The final filter may contain the filtration resin in a batch container, or in a flow cartridge, or even in a flow cartridge comprising a flow diversion valve to reintroduce a water wash in said flow cartridge multiple times in order to thoroughly was the filtration resin.

According to some embodiments, the final extract may be eluted from the filtration resin with a solution chosen from ethanol, or an alkaline aqueous solution. According to an embodiment, the sugar fraction is eluted from the final filter 290/390 with water.

Drying

Three streams of product are coming out of the process.

a) Ultrafiltration retentate: this stream contains pectin, fibers and ash. This product can be dried separately, or combined with the fiber.

b) Separator heavy slurry: this product contains fibers and ashes and has been successfully dried with a spray dryer. The operating temperature of the dryer can be high since the product is not going to be used for any other applications and no specific functionality is to be protected.

c) Polyphenol extract: If the product is not purified (85% sugars), it needs to be dried with a carrier (such as maltodextrins) to avoid crystallization in the dryer.

According to an embodiment, the process further includes the step of drying the concentrated permeate with a carrier, for obtaining a dried concentrated permeate. The carrier may be a food product having a glass transition temperature higher than a drying temperature of the concentrated permeate, such as a maltodextrin.

According to another embodiment, the process further includes the step of drying the final extract with a carrier, for obtaining a dried final extract. The carrier may be a food product having a glass transition temperature higher than a drying temperature of said concentrated permeate, such as a maltodextrin.

Products

The products that may be obtained from the process of the present invention include:

1) A concentrated permeate. The concentrated permeate may have a concentration from about 13.5% Brix to about 60% Brix when reverse osmosis and/or vacuum evaporation is used. The concentration may be from about 50% Brix to about 60% Brix, when vacuum evaporation is used, alone or in combination with reverse osmosis. The concentrated permeate may have a concentration from about 20% Brix to about 25% Brix, when reverse osmosis is used. See FIGS. 1, 3 and 6.

2) A dried concentrated permeate.

3) A final extract and/or a dried final extract. The final extract may have a concentration of up to about 85% in polyphenols on a dry weight basis.

4) A sugar fraction. The sugar fraction may have a concentration of about 95% fructose DWB, and about 5% sucrose DWB. The sugar fraction may be eluted from the final filter through washes with water, prior to the elution of the polyphenol adsorbed thereon. A concentrated sugar fraction may be obtained after concentration of the sugar fraction from the filter.

5) A fiber of said source of fruit or vegetable matter.

6) A dried fiber.

7) A retentate or dried retentate. The retentate comprises principally pectin, as well as a soluble retentate fraction.

8) A dried retentate and fiber combination.

9) A combination of any of the above products.

Expected Yield and Extract Production

Using data obtained from the pilot testing (see examples below) and lab information from NIS, the yield has been assessed. According to NIS Lab, the phenol concentration in the DAPP is 7.2 mg GAE/g of sample. Table 1 shows a quick mass balance on the process. Due to the method of analysis error, the yields are anywhere higher than 77%. This was achieved using only 2 washes (permeate 1 and permeate 2).

TABLE 1

Yields obtained during pilot tests

|  | Mass | Phenol content | Total mass of phenols |
| --- | --- | --- | --- |
| Powder in | 25 kg | 7.20 mg/g | 180 g ± 24 g |
| Permeate 1 | 135 kg | 0.55 mg/g | 74 g ± 4 g |
| Permeate 2 | 290 kg | 0.40 mg/g | 117 g ± 20 g |
| Total out |  |  | 181 g ± 24 g |

|  | Min | Center | Max |
| --- | --- | --- | --- |
| Yield | 77% | 101% | 131% |

For the full scale process (350 kg/h DAPP) using the lower yield value, the total production of 60% Brix extract with 4% DWB polyphenols would be around 80 kg/h. It represents 143 tons/y of 60% Brix extract (4% DWB phenols). Assuming 100% yield, the total extract production would be 187 tons/y at 60 Brix. Thus, the expected extract production rate lies between these two bounds. In fact, the process of the present invention which deals with 3 stages of extraction, will definitely increase the overall yield.

Expected Services and Utility Loads

Based on the pilot plant results, the preliminary process requirements are presented below. This table gives an approximation of the expected loads and requires more detailed engineering to get more accurate estimation.

TABLE 2

Expected utility loads and product streams. These are estimation and some loads could change.

|  | Hourly load |  | Annual load |  |
| --- | --- | --- | --- | --- |
| Water consumption | 18 602 | kg/h | 33 484 | m3/year |
| Electricity |  |  |  |  |
| Separators | 60 | kW |  |  |
| Reverse osmosis | 150 | kW |  |  |
| Ultrafiltration | 50 | kW |  |  |
| Fiber dryer | 300 | kW |  |  |
| Electricity - total | 560 | kW | 1 008 000 | kWh/year |
| Natural Gas - Fiber dryer | 1 162 | m3/h | 2 090 747 | m3/year |
| Inputs |  |  |  |  |
| DAPP feed | 350 | kg/h | 630 000 | kg/y |
| Extract - 60 brix | 81 | kg/h | 145 529 | kg/y |
| Retentate powder - enriched pectin powder (@ 95% solids) | 33 | kg/h | 60 023 | kg/y |
| Fiber powder (@ 95% solids) | 273 | kg/h | 491 990 | kg/y |

The present invention will be more readily understood by referring to the following examples which are given to illustrate the invention rather than to limit its scope.

Example 1

Pilot Study

Objectives a) Assess the yield of extraction and the effect of successive washes on overall phenol recovery;

b) Determine the feasibility of the water based extraction process;

c) Generate some product and determine the quality.

Process Scheme

During the tests, two process schemes are used as outlined in the figures below. The first test dealt with a single pass extraction, meaning that the DAPP powder is contacted once with water (5% solid fraction in solution by weight) and then separated using centrifuges. In the second test, the extracted powder is resuspended in fresh water to determine what fraction of soluble compounds can be further extracted.

Results

The mass balances for the two trials are presented in the table below.

TABLE 3

Mass balance for the single wash trial

|  | Mass kg | Solids % wt | Sugars % wt | Ash % wt |
| --- | --- | --- | --- | --- |
| DAPP Powder | 25.0 | 97.10% | 14.37% | 2.12% |
| Initial mixture | 500 | 4.32% |  |  |
| Grinds from decanter | 94 | 15.80% |  |  |
| Extract from decanter | 406 |  |  |  |
| Sludge from centrifuge | 5 | 15.68% |  |  |
| Extract from centrifuge | 401 | 2.68% |  |  |
| UF Permeate | 390 | 1.21% |  |  |
| UF Retentate | 140 | 4.63% |  |  |

TABLE 3-continued

Mass balance for the single wash trial

|  | Mass kg | Solids % wt | Sugars % wt | Ash % wt |
|---|---|---|---|---|
| Concentrated product | 20 | 8.24% | | |
| Extracted DAPP | N/A | | | |

TABLE 4

Mass balance for the two stages wash process

|  | Mass kg | Solids % wt | Sugars % wt | Ash % wt |
|---|---|---|---|---|
| DAPP Powder | 25.0 | 97.10% | 14.37% | 2.00% |
| First wash | | | | |
| Initial mixture | 500 | 4.30% | 0.64% | 0.09% |
| Grinds from decanter | 153 | 12.28% | | |
| Extract from decanter | 347[1] | 2.18% | | |
| Sludge from centrifuge | 17.6 | 6.52% | | |
| Extract from centrifuge | 329[2] | 1.61% | | |
| Permeate | 135 | 1.51% | | |
| Retentate | 138 | 1.03% | | |
| Second wash | | | | |
| Initial mixture | 500 | 3.94% | | |
| Grinds from decanter | 136 | 9.94% | | |
| Extract from decanter | 363 | 0.64% | | |
| Sludge from centrifuge | 40 | 6.52% | | |
| Extract from centrifuge | 324 | 0.87% | | |
| Permeate | 290 | 0.34% | | |
| Retentate | 34 | 1.03%[3] | | |
| Extract to evaporator | 425 | 0.90% | 0.68% | 0.06% |
| Concentrated product | 12 | 14.60% | 11.05% | 0.93% |
| Extracted DAPP | 7 | 97.48% | 4.21% | 1.39% |

[1]From calculations
[2]From calculations
[3]The value was not measured but assumed similar to the previous tests Site Observations a) During the operation of the decanter centrifuge, the weir plates are adjusted in order to determine the maximum solids reachable in the solid discharge along with the expected carry-over of particles in the centrate. Even though a solid concentration of 15.8% is reached the first day, the slurry has a thick and smooth liquid texture and it is difficult to obtain recognizable solid flakes or lumps in the solid discharge.

b) The product pH is rather constant between pH 4.2 and pH 4.5 during the tests.

No change in pH are noticed during the extraction process, which indicates minimal microbial growth.

c) Suspension of powder in the stirred tank is generating a lot of fine particles because the powder is fluffy. It is preferable to have a venture type of powder blender to minimize powder dust formation. Once in water, the powder forms small lumps that disintegrate after about 5-10 minutes when recirculating.

d) The grinds or thick slurry obtained from the decanter have a shear thinning behavior, meaning that its viscosity decreases when more shear is applied to it.

e) The UF permeate has a light yellow color. When about 12 inches of liquid is in the permeate tank, a red color can be seen when looking from the top of the tank.

f) The retentate has a viscous opaque texture. Further analysis will reveal that the majority of the DAPP pectin ends up in the retentate.

g) The permeate does foam slightly, especially at cold temperature (4-6° C.).

h) Some foaming is observed when operating the vacuum evaporator. Some product is lost due to entrainment, but it is believed that it is due principally to technical issues with the evaporator used for the test that does not drain the condenser properly and causes intermittent and rapid pressure drops which results in foaming. In fact, when the evaporator is running steadily, not foam was observed.

i) Concentrated product has a strong and dark red color. The smell recalls cherries and cranberries.

j) Spray drying of the concentrated extract from the evaporator failed due to the high concentration of sugars in the solution (80-85% on a dry weight basis). To solve this issue, few alternatives: 1) use of a carrier to dry the extract, 2) sell the extract in aqueous solution at 60-70% Brix concentration, 3) Remove the sugars with a resin and dry the sugar free extract.

Analysis and Discussion

The phenolic compounds are tested using the Folin reagent method. Folin-Ciocalteu method is an approximate method which tracks phenolics in a solution.

According to this method, the phenolic concentration in the extract at 13.5% Brix is shown to be around 4%-5% on a dry weight basis. The method seems to be consistent as it yields the same dry weight basis fraction of phenols in the ultra-filtration permeate, the 10% Brix and the 13.5% Brix samples. When performing a complete assay of sugars and ashes, about 17.95% of the dry weight material is found to be composed of other chemicals, which in part consists of phenols. It then means there is between 12% and 13% of the dry weight material which is unknown.

As an hypothesis for this unknown compound, it is suspected that some low molecular pectin compounds may have gone through the ultrafiltration membranes. This is supported by the fact that when resins are used to remove the phenolic compounds, the total of others compounds found in the leftover extract are 13.88% on a dry weight basis. See the trials with 2 bed volumes (By). In fact, the higher ratio, the less phenols are captured. Thus, using the 2 BV results ensures all the phenolics are in fact removed from the solution. Assuming that all the phenolics are taken out of this extract after contacting the resin, and knowing that the initial solution fed to the resin was the same identical 13.5% Brix solution, the total phenolic compounds in the initial extract can be confirmed to be 4.07% DWB (the difference between 17.95% and 13.88%).

Finally, the use of resins has a positive impact on the concentration of phenolics on a dry weight basis. In fact, looking at Table 5, the eluted solution from the resins contained around 82.5% phenols, 15% sugars and 2.5% ashes on a dry weight basis.

The elution is performed with ethanol, however it is believed an alkaline aqueous solution can be used instead to minimize operational risks and costs. It is anticipated that using an alkaline solution would increase the level of ashes in the extract when compared to elution with ethanol. The fraction of "others" in the DAPP powder and extracted DAPP powder consist of pectin, phenols and fibers. It is not possible to determine properly the fraction of each at this time.

TABLE 5

Summary of the results obtained.

| | DAPP Powder | | | | | | | |
|---|---|---|---|---|---|---|---|---|
| | DAPP Powder | Resin 2 BV Extract | Resin 2 BV Residual | Resin 12 BV Extract | Resin 12 BV Residual | Ultrafiltration permeate extract | DAPP extract 13.5 brix | Extracted DAPP Powder |
| | | | | Sample # | | | | |
| | EXP 1-1 | Res 1 | Res 2 | Res 3 | Res 4 | EXP 2-20 | EXP 2-18 | EXP 2-19 |
| Water and volatiles | 2.90% | 99.50% | 90.20% | 99.60% | 86.80% | 99.10% | 85.40% | 2.52% |
| Sugar Profile by HPLC | | | | | | | | |
| Glucose | 2.24% | 0.01% | 1.11% | 0.01% | 2.00% | 0.13% | 2.28% | 0.85% |
| Fructose | 6.52% | 0.03% | 3.61% | 0.03% | 5.17% | 0.37% | 5.97% | 2.22% |
| Sucrose | 5.61% | 0.03% | 1.59% | 0.02% | 2.33% | 0.18% | 2.80% | 1.14% |
| Maltose | 0.00% | 0.00% | 0.00% | 0.00% | 0.00% | 0.00% | 0.00% | 0.00% |
| Lactose | 0.00% | 0.00% | 0.00% | 0.00% | 0.00% | 0.00% | 0.00% | 0.00% |
| Total | 14.37% | 0.07% | 6.31% | 0.06% | 9.50% | 0.68% | 11.05% | 4.21% |
| Total sugar % | 14.37% | 0.07% | 6.31% | 0.06% | 9.50% | 0.68% | 11.05% | 4.21% |
| Ashes % | 2.12% | 0.01% | 2.13% | 0.01% | 1.25% | 0.06% | 0.93% | 1.39% |
| Others % | 80.61% | 0.42% | 1.36% | 0.33% | 2.45% | 0.16% | 2.62% | 91.88% |
| Total sugars (dwb %) | 14.80% | 14.00% | 64.39% | 15.00% | 71.97% | 75.56% | 75.68% | 4.32% |
| Ashes (dwb %) | 2.18% | 2.00% | 21.73% | 2.50% | 9.47% | 6.67% | 6.37% | 1.43% |
| Others (dwb %) | 83.02% | 84.00% | 13.88% | 82.50% | 18.56% | 17.78% | 17.95% | 94.26% |
| Total | 100.00% | 100.00% | 100.00% | 100.00% | 100.00% | 100.00% | 100.00% | 100.00% |

Example 2

Second Pilot Study

Purpose

The purpose of the tests in of this second pilot study is to determine:

a) Whether a nozzle centrifuge can be used for the counter-current wash, as opposed to an arrangement of decanter and intermittent discharge centrifuge used at the CRDA facility.

b) Confirm the membrane size selection for ultrafiltration and reverse osmosis.

c) Identify the scale-up risks and assess the operability of the process at larger scale.

Centrifuge Tests

Tests are performed with a DX203 test machine. In the first set of tests, 0.8 mm nozzles are used. Operating flow of 350 and 450 L/h give a centrate with solid concentration of 0.7% vol. and 1% vol., respectively. The nozzles are washed after 80 kg of solution is pumped in with room temperature water during 30 min at 450 L/h.

The nozzles are all clean and flowing. There is no build-up in nozzle channels, nozzles flow pockets formed evenly.

The second test is set up to determine the maximum concentration achievable in the concentrate stream. 0.7 mm nozzles are used. Results are shown in Table 6. Results show that it is possible to increase the concentration of the extract by reducing the flow through the nozzles.

TABLE 6

Pilot separator tests results with 0.7 mm nozzles.

| | Centrate | | | Concentrate | | |
|---|---|---|---|---|---|---|
| Feed rate (L/h) | Flowrate (L/h) | wt % | vol % | Flowrate (L/h) | wt % | vol % |
| 350 | 121.74 | 0.109% | 0.50% | 228.26 | 7.61% | 35% |
| 350 | 107.69 | 0.109% | 0.50% | 242.31 | 7.17% | 33% |

TABLE 6-continued

Pilot separator tests results with 0.7 mm nozzles.

| | Centrate | | | Concentrate | | |
|---|---|---|---|---|---|---|
| Feed rate (L/h) | Flowrate (L/h) | wt % | vol % | Flowrate (L/h) | wt % | vol % |
| 440 | 176.71 | 0.141% | 0.65% | 263.29 | 8.26% | 38% |
| 440 | 190.33 | 0.152% | 0.70% | 249.67 | 8.70% | 40% |
| 510 | 279.88 | 0.174% | 0.80% | 230.12 | 10.87% | 50% |
| 510 | 361.64 | 1.522% | 7.00% | 148.36 | 13.48% | 62% |
| 450 | 289.57 | 0.543% | 2.50% | 160.43 | 13.04% | 60% |
| 375 | 199.04 | 0.196% | 0.90% | 175.96 | 10.43% | 48% |

In order to verify the impact of changing the nozzle size, 0.6 mm nozzles are used. This usually allows generating a more concentrated heavy phase. The results obtained are presented in Table 7. The results show it is possible to achieve high solids with minimum entrainment in the light phase (centrate).

TABLE 7

Pilot separator tests results with 0.6 mm nozzles.

| | Centrate | | | Concentrate | | |
|---|---|---|---|---|---|---|
| Feed rate | Flowrate (l/h) | wt % | vol % | Flowrate (l/h) | wt % | vol % |
| 330 | 141.67 | 0.087% | 0.40% | 188.33 | 8.70% | 40% |
| 340 | 155.29 | 0.087% | 0.40% | 184.71 | 9.13% | 42% |
| 390 | 198.01 | 0.152% | 0.70% | 191.99 | 10.00% | 46% |
| 420 | 230.96 | 0.196% | 0.90% | 189.04 | 10.87% | 50% |

The samples of concentrate are collected (4 L) and sent for spray drying tests.

The machine is then washed with room temperature water for 20 minutes at 480 L/min. The nozzles are all clean and flowing, however there is some build-up in two nozzle channels. Nozzle flow pockets are formed evenly.

Membrane Filtration Tests

In this test, three types of spiral membranes are tested in order to see their efficiency and resistance to solids fouling. The results obtained with the two different membranes types are shown in Table 8 and Table 9. Basically, the membranes ETNA10PP-6338/48 and 6338/80 are selected because they provided a better results with solids than other membranes.

Tests on the retentate of the ultrafiltration skid have revealed presence of pectin. The retentate is put in ethanol 95% with a ratio of 2:1 ethanol to retentate. The solution containing jellified pectin is kept homogeneous before being centrifuged. The mass of gel is then removed and dried. Assuming the total mass of gel is pectin, the total concentration of pectin in the retentate is about 1.04% wt. It also represents a fraction of nearly 62% pectin on a dry weight basis.

Reverse Osmosis Tests

Reverse osmosis is tested in order to determine if it could be used in replacement of an evaporator to concentrate the extract. Results are shown in Table 10. The advantages are that it would maintain the product to a lower temperature during the concentration stage as opposed to a conventional vacuum evaporation unit.

The results show that a maximum of 20% Brix is reached at 40 bars operating pressure. This concentrated extract is sent for drying tests.

TABLE 8

Results with the ETNA10PP-3838/80 membranes.

| Membrane type: | Code No.: | Area: m² | Serial no.: | Comments: |
|---|---|---|---|---|
| ETNA10PP-3838/80 | 517508 | 3.41 | DK00133969 | ETNA10PP-3838/80 |

Start time mm:hh 09:17

| | | | Customer Product | | | Test manager | | Analysis Concentrate |
|---|---|---|---|---|---|---|---|---|
| Note: | Time mm:hh | Elapsed time mm:hh | P(in) bar | P(out) bar | TMP bar | Delta P bar | Temp. ° C. | NMN VCF |
| WF 22-2-12 | 11:19 | | 2.6 | 1.5 | 2.05 | 1.1 | 22 | |
| recirl. 23-2-12 | 08:40 | | 4.5 | 3.2 | 3.85 | 1.3 | 13 | |
| Start concentration | 09:17 | 00:00 | 4.5 | 3.3 | 3.9 | 1.2 | 24 | 1 |
| | 09:48 | 00:31 | 4.6 | 3.3 | 3.95 | 1.3 | 27 | 1.0948 |
| | 10:31 | 01:14 | 4.5 | 3.2 | 3.85 | 1.3 | 24 | 1.2486 |
| | 11:17 | 02:00 | 4.5 | 3.2 | 3.85 | 1.3 | 25 | 1.4259 |
| | 11:37 | 02:20 | 4.5 | 3.2 | 3.85 | 1.3 | 25 | 1.5049 |
| | 11:57 | 02:40 | 4.5 | 3.2 | 3.85 | 1.3 | 24 | 1.3621 |
| | 12:47 | 03:30 | 4.5 | 3.2 | 3.85 | 1.3 | 25 | 1.4908 |
| | 13:15 | 03:58 | 4.6 | 3.2 | 3.9 | 1.4 | 25 | 1.5742 |
| | 14:01 | 04:44 | 4.6 | 3.2 | 3.9 | 1.4 | 25 | 1.7162 |
| | 14:50 | 05:33 | 4.6 | 3.2 | 3.9 | 1.4 | 25 | 1.8918 |
| | 15:28 | 06:11 | 4.7 | 3.2 | 3.95 | 1.5 | 25 | 2.0346 |
| | 16:24 | 07:07 | 4.7 | 3.1 | 3.9 | 1.6 | 24 | 2.2943 |
| | 17:02 | 07:45 | 4.7 | 3.1 | 3.9 | 1.6 | 24 | 2.4789 |
| stop | 17:33 | 08:16 | 4.7 | 3 | 3.85 | 1.7 | 24 | 2.6626 |
| WF 24-2-12 Recovery | 10:47 | | 2.6 | 1.5 | 2.05 | 1.1 | 22 | |

| Membrane type: ETNA10PP-3838/80 | | | | Comments: ETNA10PP-3838/80 | | | | |

Start time mm:hh 09:17

| | Analysis Concentrate | | | | Analysis Permeate | | | |
|---|---|---|---|---|---|---|---|---|
| Note: | Cross-flow m³/h | Brix | Flux l/h | Flux l/m²/h | Brix | Feed vol I | Perm vol I | Dia vol I | Sample ID |
| WF 22-2-12 | | | 295 | 86.51 | | | | | |
| recirl. 23-2-12 | 11.9 | | 83 | 24.34 | | 462 | | | |
| Start concentration | 11.9 | 1.8 | 85 | 24.927 | 1.4 | 462 | 0 | | M |
| | 11.9 | | 78 | 22.874 | | 462 | 40 | | |
| | 11.8 | | 64 | 18.768 | | 462 | 92 | | |
| | 11.7 | | 54 | 15.836 | | 462 | 138 | | |
| | 11.7 | | 51 | 14.956 | | 462 | 155 | | |
| | 11.7 | | 50 | 14.663 | | 647 | 172 | | |
| | 11.7 | | 48 | 14.076 | | 647 | 213 | | |
| | 11.7 | 2 | 46 | 13.49 | 1.3 | 647 | 236 | | N |
| | 11.7 | | 44 | 12.903 | | 647 | 270 | | |
| | 11.6 | | 41 | 12.023 | | 647 | 305 | | |
| | 11.6 | | 39 | 11.437 | | 647 | 329 | | |
| | 11.5 | 2 | 37 | 10.85 | 1.5 | 647 | 365 | | O |
| | 11.4 | | 36 | 10.557 | | 647 | 386 | | |

TABLE 8-continued

Results with the ETNA10PP-3838/80 membranes.

| | | | | | | | | | |
|---|---|---|---|---|---|---|---|---|---|
| stop | | 11.1 | 2.5 | 35 | 10.264 | 1.5 | 647 | 404 | P |
| WF 24-2-12 | | | | 297 | 87.097 | | | | |
| Recovery | | | | | 101% | | | | |

TABLE 9

Results obtained with GR60PE membranes.

| Membrane type: | Code No.: | Area: m² | Batch no.: | Comments: |
|---|---|---|---|---|
| GR60PE | | 0.1044 | 10472-? | GR60PE |

Start time mm:hh

| | | Customer Product | | Test manager | | | Analysis Concentrate | |
|---|---|---|---|---|---|---|---|---|
| Note: | Time mm:hh | Elapsed time mm:hh | P(in) bar | P(out) bar | TMP bar | Delta P bar | Temp. °C. | NMN VCF | Cross-flow l/h |
| WF | 13:00 | | 2.4 | 1.7 | 2.05 | 0.7 | 20 | | 480 |
| | 13:17 | | 3.8 | 2.3 | 3.05 | 1.5 | 20 | | 480 |
| | 13:34 | | 3.8 | 2.3 | 3.05 | 1.5 | 20 | 1 | 480 |
| | 14:13 | | 3.8 | 2.3 | 3.05 | 1.5 | 20 | 1 | 480 |
| | 15:21 | | 5.2 | 2.2 | 3.7 | 3 | 20 | | 480 |
| stop | 15:27 | | 7 | 4 | 5.5 | 3 | 20 | 2.3333 | 480 |
| | | | | | 0 | 0 | | | 480 |
| | 16:17 | | 2.4 | 1.7 | 2.05 | 0.7 | 20 | | 480 |
| | | | | | 0 | 0 | | | 8 |

| Membrane type: | | | | | Comments: | | | |
|---|---|---|---|---|---|---|---|---|
| GR60PE | | | | | GR60PE | | | |

Start time mm:hh

| | | Analysis Concentrate | | | | Analysis Permeate | | | | |
|---|---|---|---|---|---|---|---|---|---|---|
| Note: | Brix | Abs. 286 nm | Flux ml/min | Flux /h l/m² | Brix | Abs. 286 nm | Feed vol I | Perm vol I | Sample ID |
| WF | | | 235 | 135.060 | | | | | |
| | 1.7 | | 95 | 54.593 | 1.3 | | 7 | | |
| | | | 75 | 43.103 | | | 7 | 0 | A |
| | | | 46 | 26.437 | | | 7 | | |
| stop | 2.2 | 10.7 | 50 | 28.736 | 1.4 | 9.7 | 7 | 4 | B |
| | | | | 0 | | | | | |
| | | | 105 | 60.345 | | | | | |
| | | | | 45% | | | | | |

TABLE 10

Results with the reverse osmosis RO98pHt-3838/48 membranes.

| Membrane type: | Code No.: | Area: m² | Serial no.: | Comments: |
|---|---|---|---|---|
| RO98pHt-3838/48 | 516646 | 4.71 | DK00139629 | RO98pHt-3838/48 |

Start time mm:hh

| | | Customer Product | | | Test manager | | | Analysis Concentrate | | |
|---|---|---|---|---|---|---|---|---|---|---|
| Note: | Time mm:hh | Elapsed time mm:hh | P(in) bar | P(out) bar | TMP bar | Delta P bar | Temp. °C. | NMN VCF | Cross-flow m³/h | Brix |
| WF 23-2-12 | 10:53 | | 16 | 15 | 15.5 | 1 | 26 | | 6.7 | |
| start recirl | 11:08 | | 31 | 30 | 30.5 | 1 | 23 | | 6.5 | |

TABLE 10-continued

Results with the reverse osmosis RO98pHt-3838/48 membranes.

| | Start time mm:hh | | | | | | | | |
|---|---|---|---|---|---|---|---|---|---|
| start conc. | 14:33 | 31 | 30 | 30.5 | 1 | 21 | 1 | 6.4 | 1.1 |
| | 14:48 | 31 | 30 | 30.5 | 1 | 21 | 1.697 | 6.4 | |
| | 15:27 | 31 | 30 | 30.5 | 1 | 22 | 3.2576 | 6.4 | |
| | 16:31 | 31 | 30 | 30.5 | 1 | 22 | 5.6833 | 6.4 | 5.7 |
| | 17:00 | | 30 | 29.5 | 29.75 | 0.5 | 22 | 10.114 | 4 |
| stop | 17:24 | 24 | 23.5 | 23.75 | 0.5 | 22 | 11.733 | 2 | 11.6 |
| WF 24-2-12 Recovery | 10:10 | 16 | 15 | 15.5 | 1 | 26 | | 7.1 | |

| Membrane type: | Comments: |
|---|---|
| RO98pHt-3838/48 | RO98pHt-3838/48 |

| | Analysis Concentrate | | | | Analysis Permeate | | | | | |
|---|---|---|---|---|---|---|---|---|---|---|
| Note: | Conductivity µS/cm | Flux l/h | Flux l/m²/h | Brix | Conductivity µS/cm | % PM | Feed vol I | Perm vol I | Dia vol I | Sample ID |
| WF 24-2-12 | 4330 | 174 | 36.943 | | 94.7 | 2% | | | | |
| start recirl | | 240 | 50.955 | | | | 66 | 0 | | |
| start conc. | | 187 | 39.703 | 0.1 | | | 66 | 0 | | S |
| | | 175 | 37.155 | | | | 112 | 46 | | |
| | | 146 | 30.998 | | | | 215 | 149 | | |
| | | 104 | 22.081 | 0.1 | | | 341 | 281 | | T |
| | | 60 | 12.739 | | | | 354 | 319 | | |
| stop | | ? | ? | | | | 352 | 322 | | U |
| WF 24-2-12 Recovery | 4360 | 149 | 31.635 86% | | 56.5 | 1% | | | | |

CONCLUSION

The pilot tests show that the proposed process works and yields polyphenol extracts between 4-6% by weight on a dry weight basis (DWB). The liquid extract can be further purified using resins to yield 85% by weight (DWB) polyphenol extract. The process of the present invention is simple as it deals with an aqueous solvent to do the extraction. Some additional engineering work will assess whether a reverse osmosis system coupled with a small evaporator system brings more significant value on a capital standpoint than using a single larger evaporator system to concentrate the extract. In this study, we have proven that both process routes are viable.

The concentrated permeate cannot be dried as is due to its large sugar content of 85% on a weight basis (DWB), mainly fructose and sucrose. However, it can be dried using a maltodextrin carrier. Also, if the concentrated permeate is purified and most of the sugars are removed, it may be dried as is. It makes sense to start the production of extracts in aqueous form, i.e. producing 60-70% Brix polyphenol extracts (4-6% phenols DWB) with the initial sugars. The sugars are natural (fructose and sucrose) and if the extract is used as an additive in food, it could bring a substantial amount of antioxidant along with natural sugars. These sugars could then replace original sugars in the former formulation of any product. Focusing on liquid concentrated extract reduces the capital cost associated with drying the extract and also simplifies the operations for startup. Moreover, this extract can be produced on a regular basis, and thus the risks are quite minimal.

Should there be a need for more purified extracts, ethanol as the eluent in the resin-based purification process would have to be replaced. The resin process is successful in purifying the polyphenols using ethanol as eluent up to 85% DWB. However, for a larger scale operation, it is preferable to use an alkaline solution to elute the polyphenols from the resin. Also, a rather high purity pectin by-product can be obtained from the process of the present invention. However, this stream contains low solid fraction which makes it expensive to dry as is. An evaporator system would be preferable to further raise the solids prior to drying to minimize operation costs.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A process for extraction of at least a polyphenol content from apple peel in a solvent with a system comprising a separator centrifuge assembly comprising
    a first, second and third nozzle centrifuge,
        said first nozzle centrifuge being both in fluid communication with, and in counter-current fluid communication with said second nozzle centrifuge, and
        said second nozzle centrifuge being both in fluid communication with, and in counter-current fluid communication with said third nozzle centrifuge; and
    an ultrafiltration unit in fluid communication with said first nozzle centrifuge, the process comprising:
    1) introducing counter-currently a second wash from said second nozzle centrifuge in a mixer and/or said first nozzle centrifuge, for extraction in said first nozzle centrifuge;
    2) introducing counter-currently a third wash from said third nozzle centrifuge in said second nozzle centrifuge, for extraction in said second nozzle centrifuge;
    3) ultrafiltering with said ultrafiltration unit a first wash from said first nozzle centrifuge to obtain a retentate and a permeate, wherein no enzymes are used for pre-treatment of said apple peel before the process of the extraction, and no enzymes are used for the process for extraction.

2. The process according to claim 1, wherein said mixer is for dissolving and decanting said apple peel, and is in fluid communication with said first nozzle centrifuge.

3. The process according to claim 2, wherein said mixer is in counter-current fluid communication with said second nozzle centrifuge.

4. The process according to claim 2, wherein said mixer comprises at least one mixing tank for dissolving and decanting said apple peel in said solvent.

5. The process according to claim 1, further comprising a solvent inlet to introduce said solvent in said separator centrifuge assembly.

6. The process according to claim 2, wherein said system further comprises a pre-filter connected between said mixer and said first nozzle centrifuge.

7. The process according to claim 1, wherein said system further comprises a fiber collector in fluid communication with said third nozzle centrifuge, for collecting a fiber from said apple peel.

8. The process according to claim 1, wherein said ultrafiltration unit comprises a first filter having a 10 kDa cutoff, for passage of particles of size 10 kDa or smaller from said first wash.

9. The process according to claim 8, wherein said system further comprises a first concentrator unit, in fluid communication with said ultrafiltration unit, for concentration of said permeate into a concentrated permeate.

10. The process according to claim 8, wherein said system further comprises a final filter for filtration of said permeate.

11. The process according to claim 9, wherein said system further comprises a second filter for filtration of said concentrated permeate and provide a final extract.

12. The process according to claim 10, wherein said system further comprises a second concentrator unit, in fluid communication with said final filter, for concentration of a sugar fraction obtained from said final filter.

13. The process according to claim 7, further comprising the steps of drying any one of said retentate and said fiber, to obtain a dried retentate and/or a dried fiber.

14. The process according to claim 11, further comprising the steps of drying any one of said final extract and said concentrated permeate, to obtain a dried final extract and/or a dried concentrated permeate.

15. The process of claim 14, wherein the step of drying said concentrated permeate is performed with a carrier.

16. The process of claim 15, wherein said carrier is chosen from a food product having a glass transition temperature higher than a drying temperature of said concentrated permeate.

17. The process of claim 14, wherein the step of drying said final extract further comprises condensing solvent from said final extract.

18. The process of claim 1, further comprising the step of reintroducing solvent in said first nozzle centrifuge, for further extraction in said first nozzle centrifuge.

19. The process of claim 9, wherein said first concentrator unit is a reverse osmosis unit, a vacuum evaporator unit, or a combination thereof.

20. The process of claim 12, wherein said second concentrator unit is at least one of a reverse osmosis unit and a vacuum evaporator unit.

21. The process of claim 1, wherein said solvent is water, an alcohol, or a combination thereof.

22. The process of claim 1, wherein said apple peel is fresh apple peel, dried apple peel, dried apple peel powder, or combinations thereof.

23. The process of claim 1, further comprising washing said retentate, for recovering a soluble fraction and pectin.

24. The process of claim 2, wherein said system further comprises a feed pump between said mixer and said first nozzle centrifuge, for pumping said apple peel in said solvent.

* * * * *